(12) United States Patent
Nentwick et al.

(10) Patent No.: US 8,607,428 B2
(45) Date of Patent: Dec. 17, 2013

(54) IMPLANTABLE CATHETER AND METHOD OF USING SAME

(75) Inventors: Brian F. Nentwick, Greenfield Center, NY (US); James Steven Kenny, Queensbury, NY (US)

(73) Assignee: AngioDynamics, Inc., Latham, NY (US)

( * ) Notice: Subject to any disclaimer, the term of this patent is extended or adjusted under 35 U.S.C. 154(b) by 406 days.

(21) Appl. No.: 13/042,722

(22) Filed: Mar. 31, 2011

(65) Prior Publication Data

US 2012/0253295 A1    Oct. 4, 2012

(51) Int. Cl.
*B23P 6/00*    (2006.01)
*A61M 25/00*    (2006.01)

(52) U.S. Cl.
USPC .................................. 29/402.01; 604/264

(58) Field of Classification Search
USPC ............ 29/402.01, 402.08, 402.09; 604/246, 604/508, 174, 43, 533
See application file for complete search history.

(56) References Cited

U.S. PATENT DOCUMENTS 7,905,875 B2 * 3/2011 Smith et al. .................. 604/508

* cited by examiner

*Primary Examiner* — John C Hong
(74) *Attorney, Agent, or Firm* — Ryan D. Artis

(57) ABSTRACT

A catheter repair kit and method for repairing a catheter is provided. The catheter repair kit can include a rod and a connection element for coupling the rod to the connection element. The method of repairing the catheter can include providing a catheter with a remnant extension leg, a replacement extension tube, and the steps of attaching a connection element to the remnant extension leg, and coupling the remnant extension leg to the replacement extension tube.

4 Claims, 23 Drawing Sheets

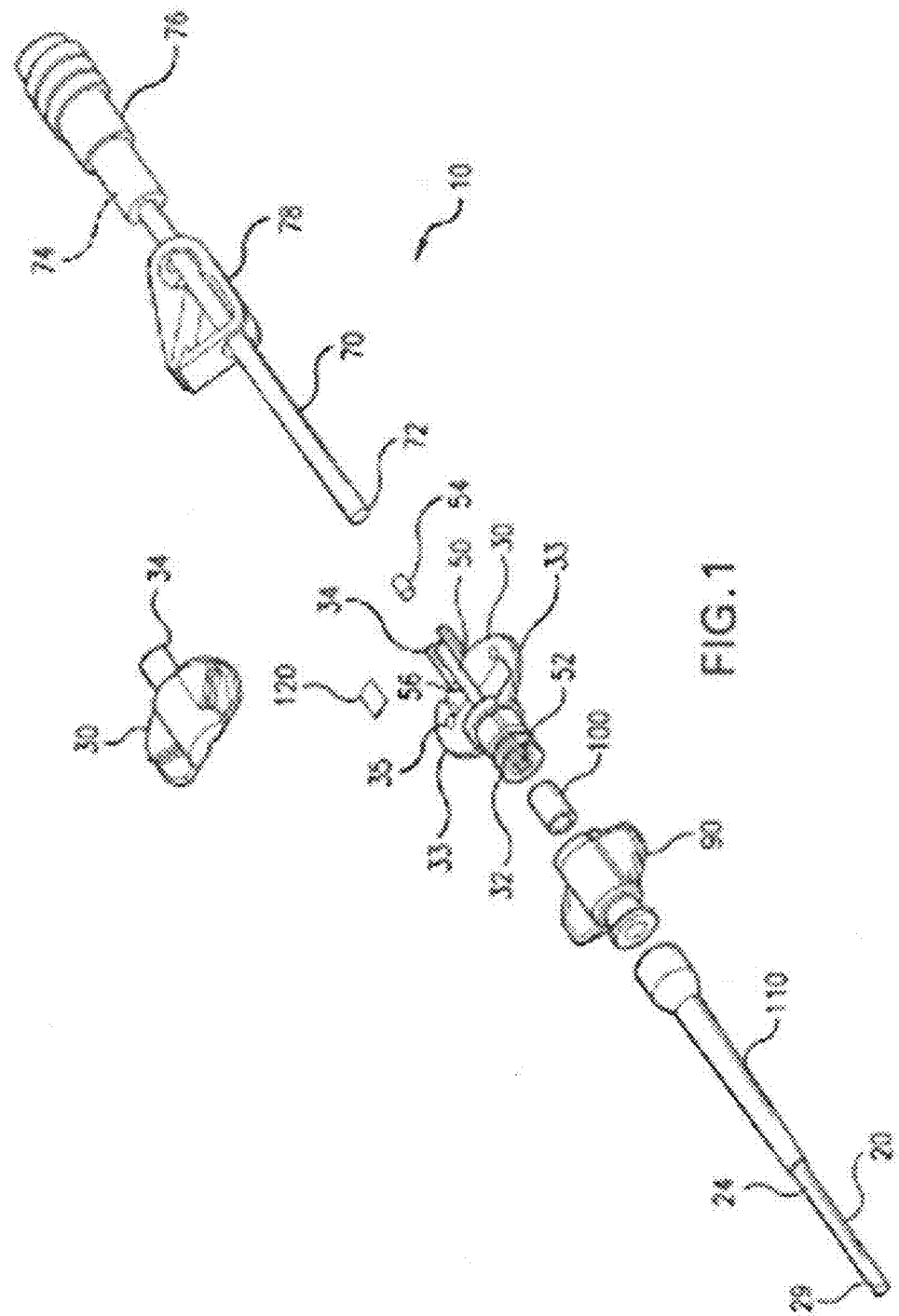

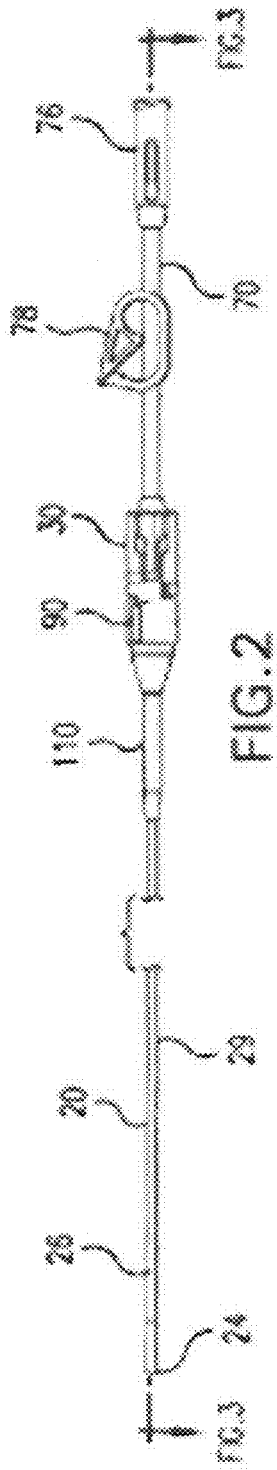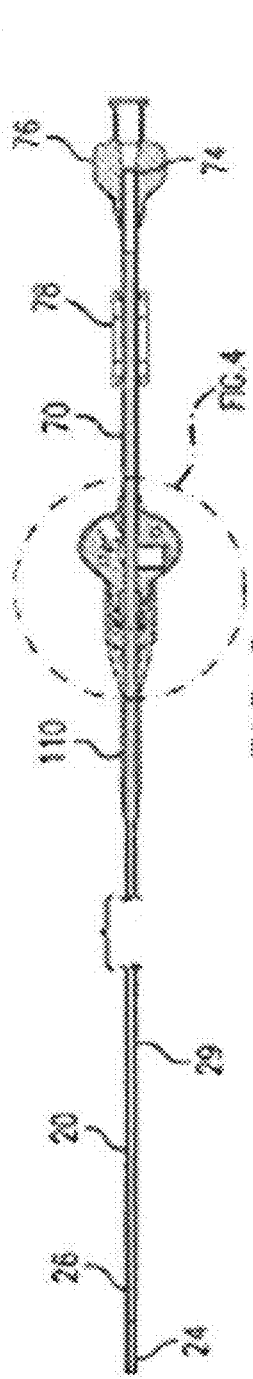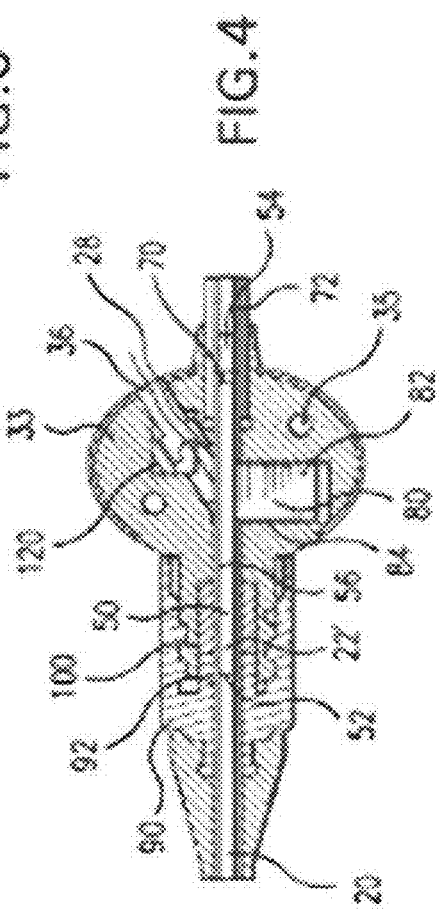

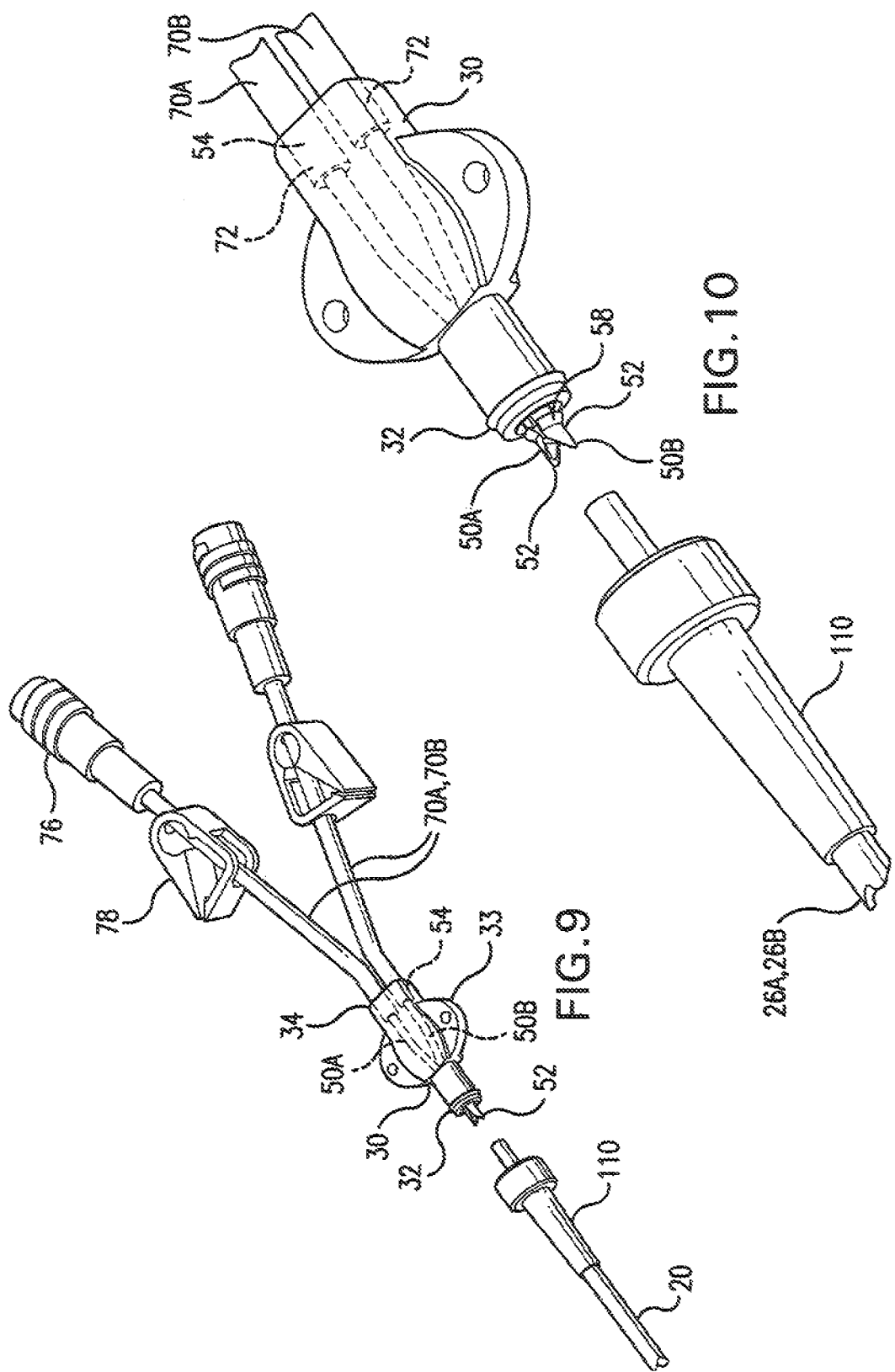

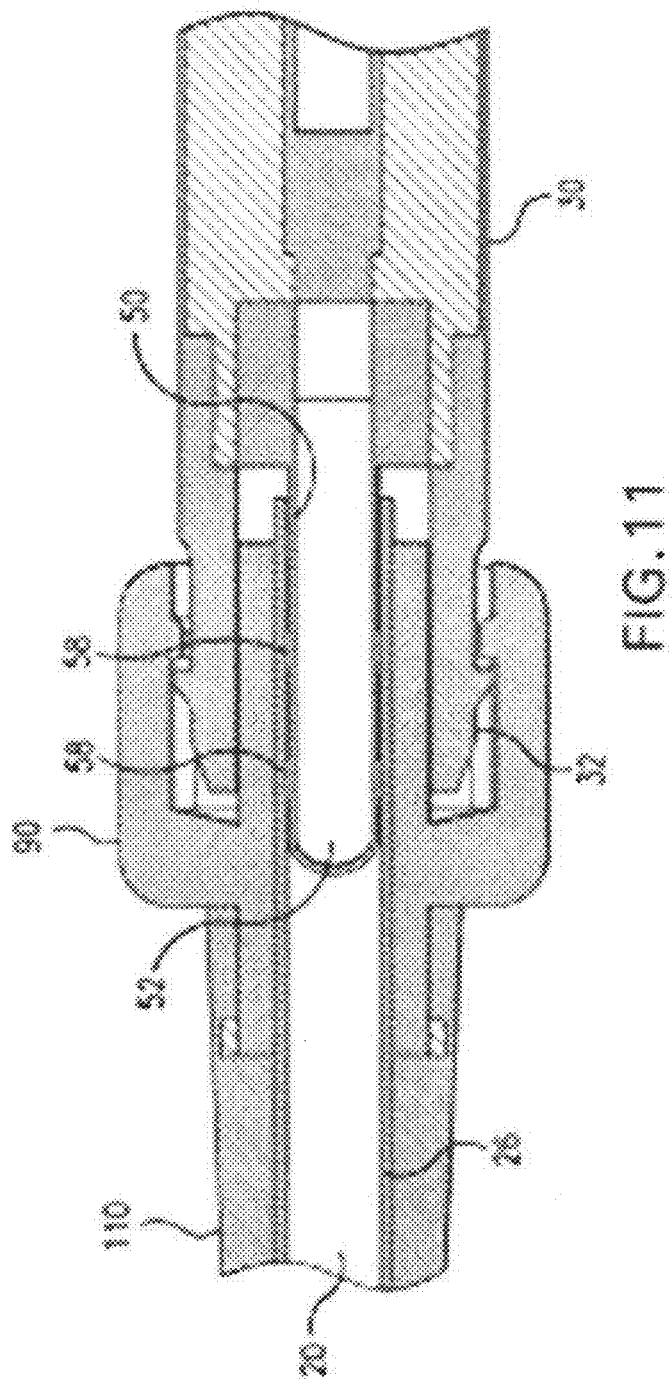

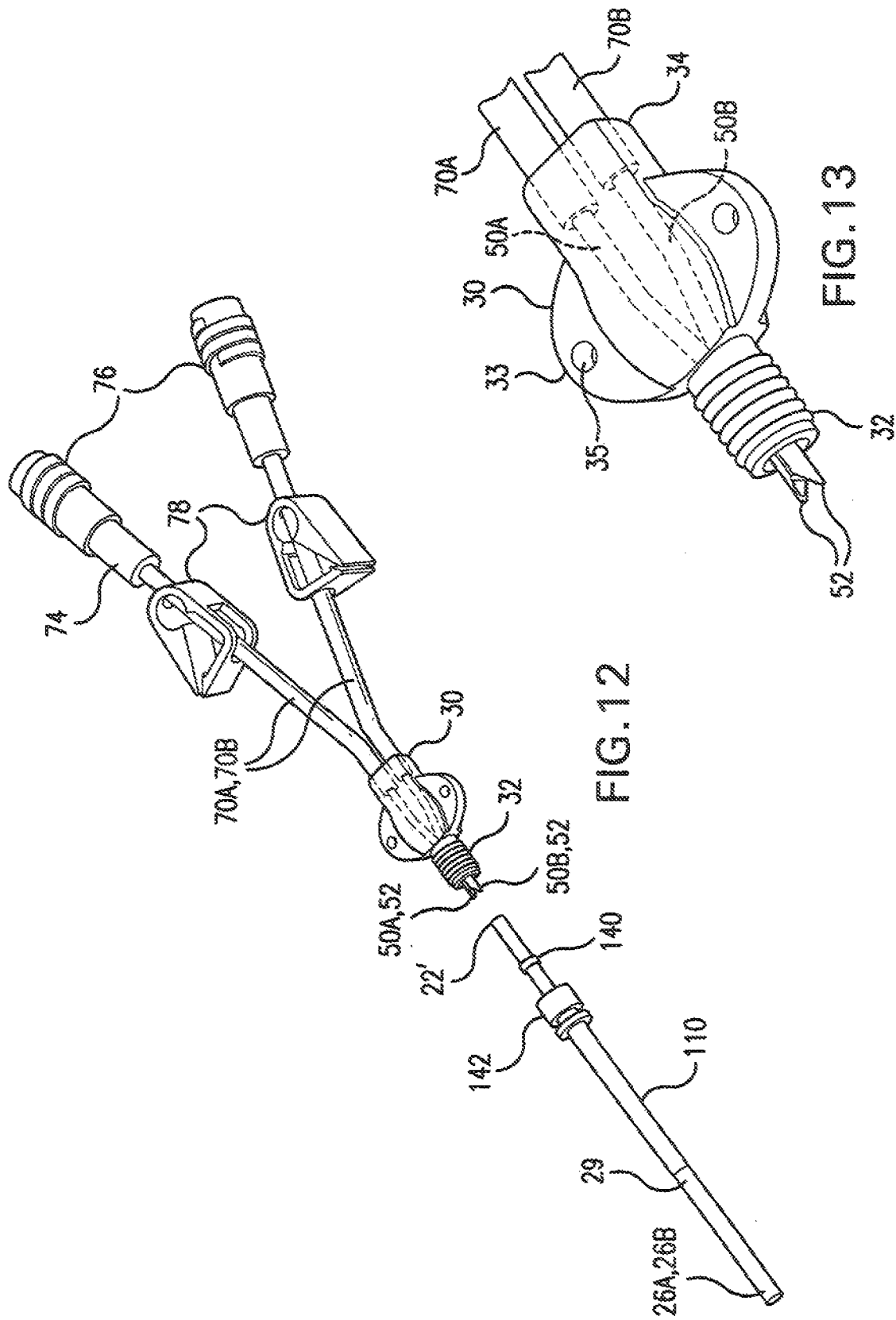

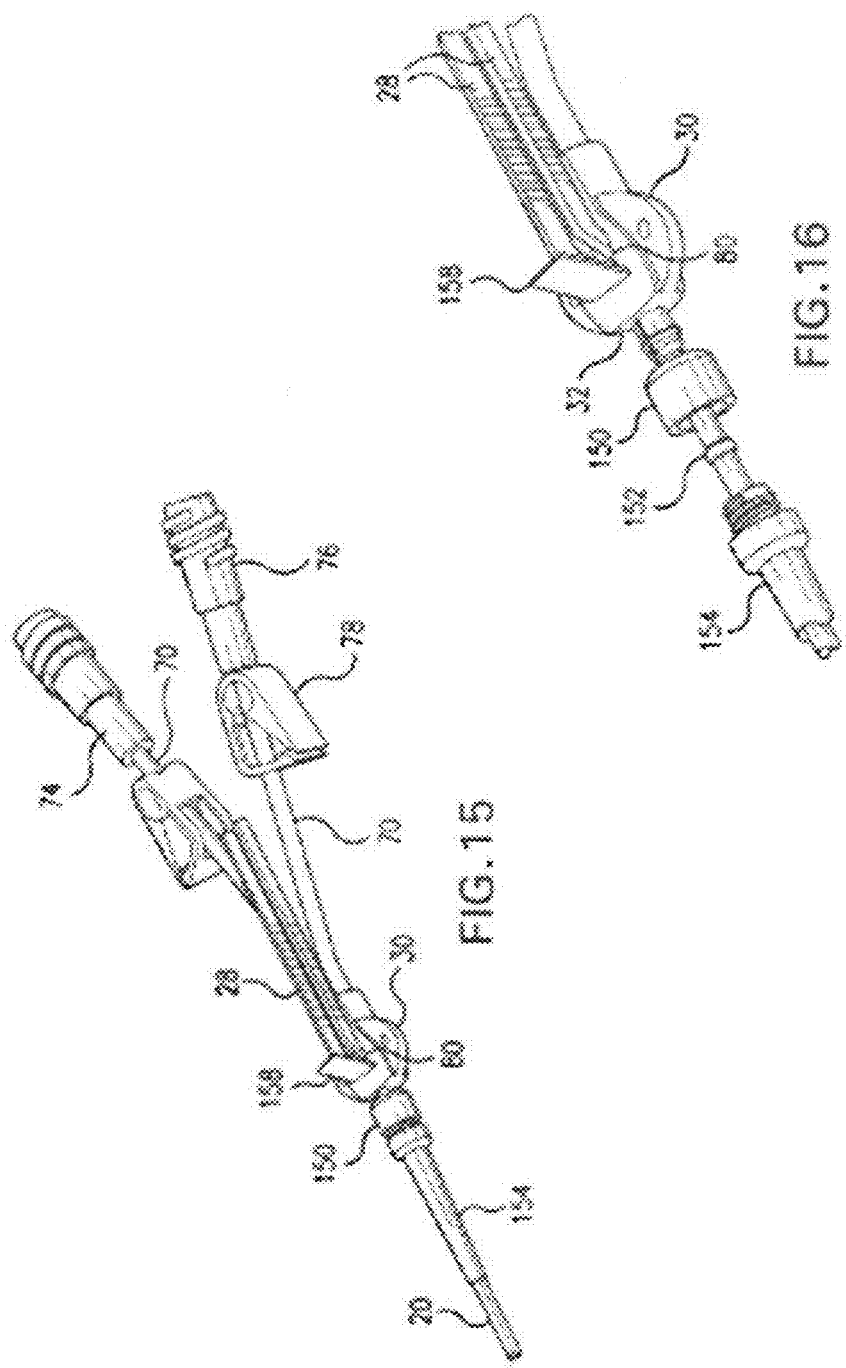

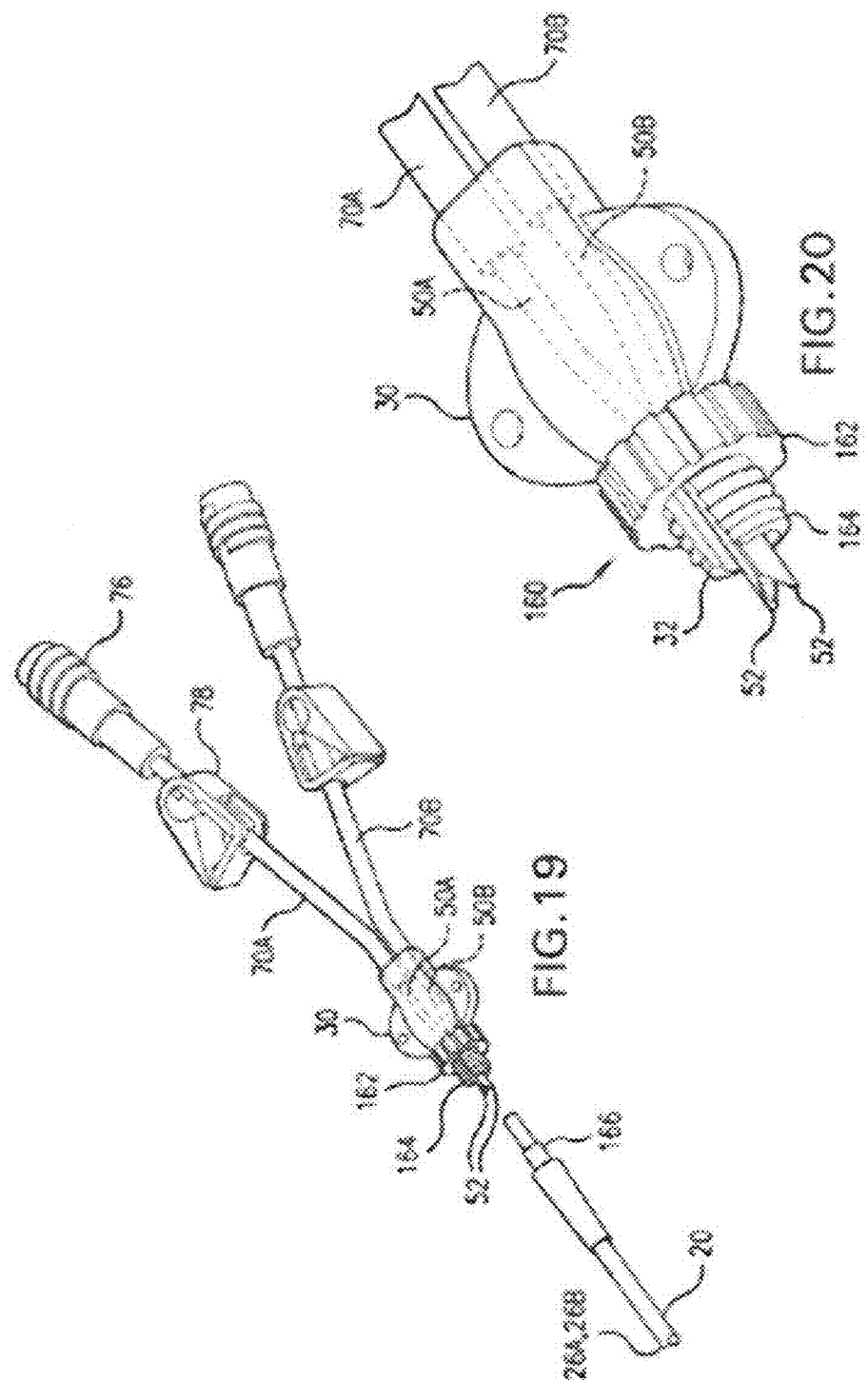

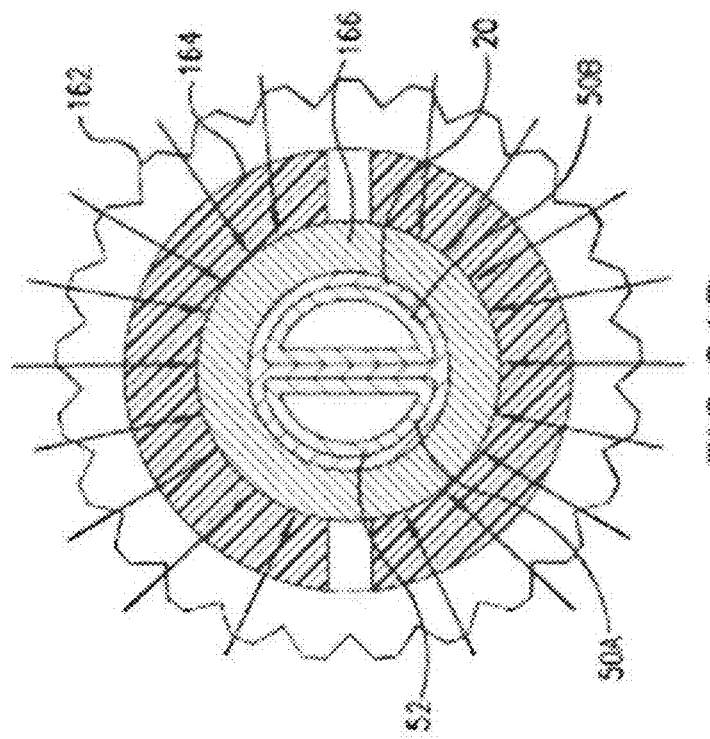
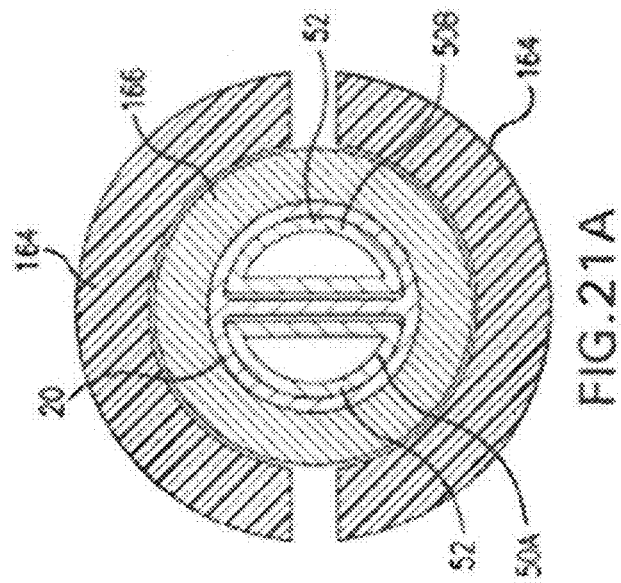

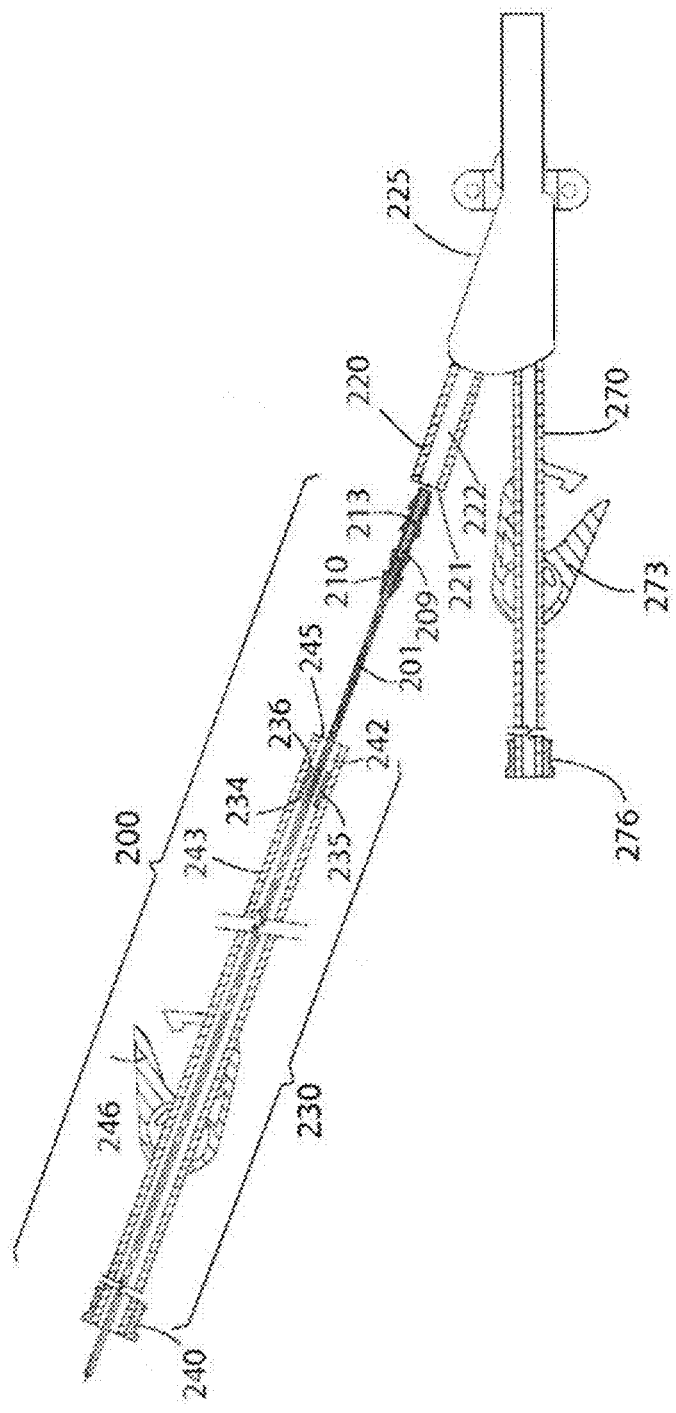

IMPLANTABLE CATHETER AND METHOD OF USING SAME

FIELD OF THE INVENTION

The invention relates in general to implantable medical devices. More particularly, the invention relates to implantable catheters, and methods of using same, that allow the catheter tube to be sized to a desired length while also allowing for the accurate placement of the tip of the catheter tube within a subject.

BACKGROUND OF THE INVENTION

The use of implantable catheters in the art of drug delivery and blood sampling is well known, in which at least one of several known types of catheters is implanted in a patient's system. These catheters are designed to provide repeated access to the vascular system of the patient for the purpose of performing drug delivery, blood sampling, and extracorporeal treatment of blood, such as hemodialysis and apheresis. The use of these devices reduces the trauma otherwise associated with multiple punctures of the venous system using needles for the same treatment purposes.

Implantable catheters are used to facilitate extracorporeal treatment of blood, frequent blood sampling, or provide for the delivery of medications, nutrition, blood products, and imaging solutions into the blood stream. Access to the catheter is typically accomplished by means of a luer lock extension attached to the distal end of the catheter assembly.

Implantable catheters are supplied as sterile devices, provided for single patient use only, and are available in a variety of materials, including polyurethane and silicone. A polyester cuff is sometimes formed on the catheter cannula to facilitate the anchorage of the catheter to the patient's underlying fascia, for example muscle. Implantable catheters are typically available in single and dual lumen models.

A major problem with implanted catheters is accurate placement of the tip of the catheter lumen. The tip must be placed very accurately in the patient's system in order to optimize the catheter's use and survivability. This is normally done by use of fluoroscopic guidance during implant and the addition of a radiopaque tip on the tip portion of the catheter tube aids greatly in accurate placement. Though there are many methods known in the art whereby a radiopaque tip may be placed on a catheter tube for better visualization during implantation, the use of these devices is limited by the fact that the hub to tip length of the catheter tube is conventionally fixed. This forces the surgeon to either use one length catheter for every sized patient, or to trim the tip portion of the catheter tube to customize the length of the catheter tube to the particular anatomical size of the patient. The use of one standard length for every patient is unattractive due to the fact that this typically results in excessive catheter tube being exposed outside the body after implant of the catheter on smaller patients. The conventional solution of cutting the catheter to the desired length removes the radiopaque tip portion of the catheter tube, which results in a loss of implant accuracy.

Further, the conventional process of determining the proper length for the tunnel (i.e., length from outside the body to the venotomy site) and the proper length catheter for placement in the vein to ensure that the tip is at the desired location is quite crude and imprecise. Typically, a physician places the catheter on the exterior of the patient's body and estimates the location of the desired site. This crude process is used by the physician to obtain the "proper" length for the catheter. A problem with this approach, however, is that it does not always provide the physician with the exact catheter tip placement that is desired.

What is needed, therefore, is an implantable catheter with the ability to have the catheter tip of the catheter tube positioned accurately via a radiopaque portion. The implantable catheter of the present invention also allows the length of the catheter tube to be customized to a desired length and attached to a hub member of the catheter to place the catheter tube into fluid communication with desired medical devices and/or solutions.

The use of repair kits to mend a damaged catheter system is well known in the art. Implantable catheters, as previously described, are typically used for an extended period of time. Some common problems that occur over extended use include weakening or breakage of an implanted catheter's clamps, luer ends, extension tubes, or the catheter body itself. Currently known in the art are repair systems that repair a broken or damaged implantable catheter but have several limitations.

A number of limitations exist with the currently known repair systems. For example, current repair systems require that the broken or damaged extension legs require a minimum length of viable extension tubing, for example at least 4.5 cm. This means that if the extension tubing is broken or damaged with less than 4.5 cm of viable tubing left then such a currently known repair kit system cannot be used. Furthermore, another limitation of currently known repair systems is a lack in durability and strength. This means current repair systems often do not have a fluid-tight fit and tend to leak, and are also made materials that have the likelihood to wear and break over time. The device described in this application solves these problems currently in the art by providing a catheter repair kit which is made out of catheter tubing, which provides for strength and durability over many uses, creates a fluid-tight seal when properly used, and also can be used with any length of exposed viable catheter tubing.

SUMMARY

The present invention is a single or dual lumen implantable catheter for allowing repeated access to a patient's system for the purpose of extracorporeal treatment of blood, frequent blood sampling, or to provide for the delivery of medications, nutrition, blood products, and imaging solutions into the blood stream.

It is contemplated that the implantable catheter of the present invention would be positioned using fluoroscopic guidance. In one aspect, the tip of the catheter tube is positioned using fluoroscopic guidance. In this aspect, at least a portion of the tip of the catheter tube is formed of a radiopaque material through means currently known in the art.

The catheter of the present invention comprises a hub member that is selectively connected to a catheter tube and at least one extension leg with a connector at its distal end for attachment to other conventional medical devices. In certain aspects the catheter comprises a hemostasis tapered plug. Alternative aspects of the catheter comprise a locking mechanism and/or attachment tube(s). The catheter of the present invention provides a conduit of user determinative length to be established between attached medical devices and the patient's internal fluid pathways.

The catheter repair kit of the present invention comprises a rod having a proximal end and a distal end, wherein the distal end of said rod is coupled to a connection element. The catheter repair kit also comprises a replacement extension tube having a fitting coupled at the proximal end of the replacement extension tube.

Other apparatuses, methods, and aspects and advantages of the invention will be discussed with reference to the Figures and to the detailed description of the preferred embodiments.

BRIEF DESCRIPTION OF THE FIGURES

The accompanying drawings, which are incorporated in and constitute a part of this specification, illustrate several aspects described below and together with the description, serve to explain the principles of the invention. Like numbers represent the same elements throughout the figures.

FIG. 1 is a partial perspective exploded view of a single lumen catheter of the present invention.

FIG. 2 is a partial side elevational view of the single lumen catheter of FIG. 1.

FIG. 3 is a partial cross-sectional view of the single lumen catheter of FIG. 1, taken across line 3-3 of FIG. 2.

FIG. 4 is an enlarged cross-sectional view of the single lumen catheter of FIG. 3.

FIG. 9 shows a partial perspective view of a third embodiment of the catheter of the present invention for a dual lumen catheter, showing a pair of extension tubes mounted to a hub member and in communication with a pair of attachment tubes mounted therein the hub member, showing a dual lumen catheter having a hemostasis taper sleeve mounted thereon, and showing a snap fit cap connected to the end of the hemostasis taper sleeve.

FIG. 10 shows an enlarged view of the hub member, hemostasis taper sleeve and snap fit cap of the catheter assembly of FIG. 9.

FIG. 11 is a partial cross-sectional view of the snap fit cap positioned in the connected position with a portion of the proximal port of the hub member, showing the barbed portion of an attachment tube engaged with a portion of the trimmed end of the dual lumen catheter.

FIG. 12 is an exploded partial perspective view of a fourth embodiment of the catheter of the present invention for a dual lumen catheter.

FIG. 13 is a partial perspective view of a hub member of the catheter of FIG. 12.

FIG. 15 is a partial perspective view of a fifth embodiment of the catheter of the present invention for a dual lumen catheter, showing waste portions of the dual lumen catheter extending from a hub member of the catheter.

FIG. 16 is an exploded partial perspective view of the catheter of FIG. 15, showing a compression ring fitting mounted thereon a portion of the dual lumen catheter proximal to the hemostasis taper sleeve and a clamping cap mounted thereon the proximal port of the hub.

FIG. 19 is a perspective view of a sixth embodiment of the catheter of the present invention for a dual lumen catheter, showing a clamping cap rotatably mounted thereto a portion of the proximal port of the hub that is adapted to selectively engage a portion of the hemostasis taper sleeve.

FIG. 20 is a partial enlarged view of the hub member of the catheter of FIG. 20.

FIGS. 21A and 21B are cross-sectional views of the means for securing the trimmed ends of the catheter lumen to the attachment tubes mounted therein the hub member.

FIG. 29 is a partial cross-sectional view of extension legs of a multi-lumen implanted catheter being repaired with a repair kit, and the hub is shown in a plan view.

FIG. 30A is a cross sectional view of the extension leg of a single lumen implanted catheter and the repair kit prior to repair.

FIG. 30B is a cross sectional view of the extension leg of a single lumen implanted catheter showing insertion of the connection element into the lumen of the extension leg.

FIG. 30C is a cross sectional view of the extension leg of a single lumen implanted catheter showing insertion of the connection element into the replacement catheter tubing.

FIG. 30D is a cross sectional view of the extension leg of a single lumen implanted catheter and repair kit illustrating the removal of the delivery rod after the repair has been completed.

DETAILED DESCRIPTION OF THE INVENTION

Figure 5:
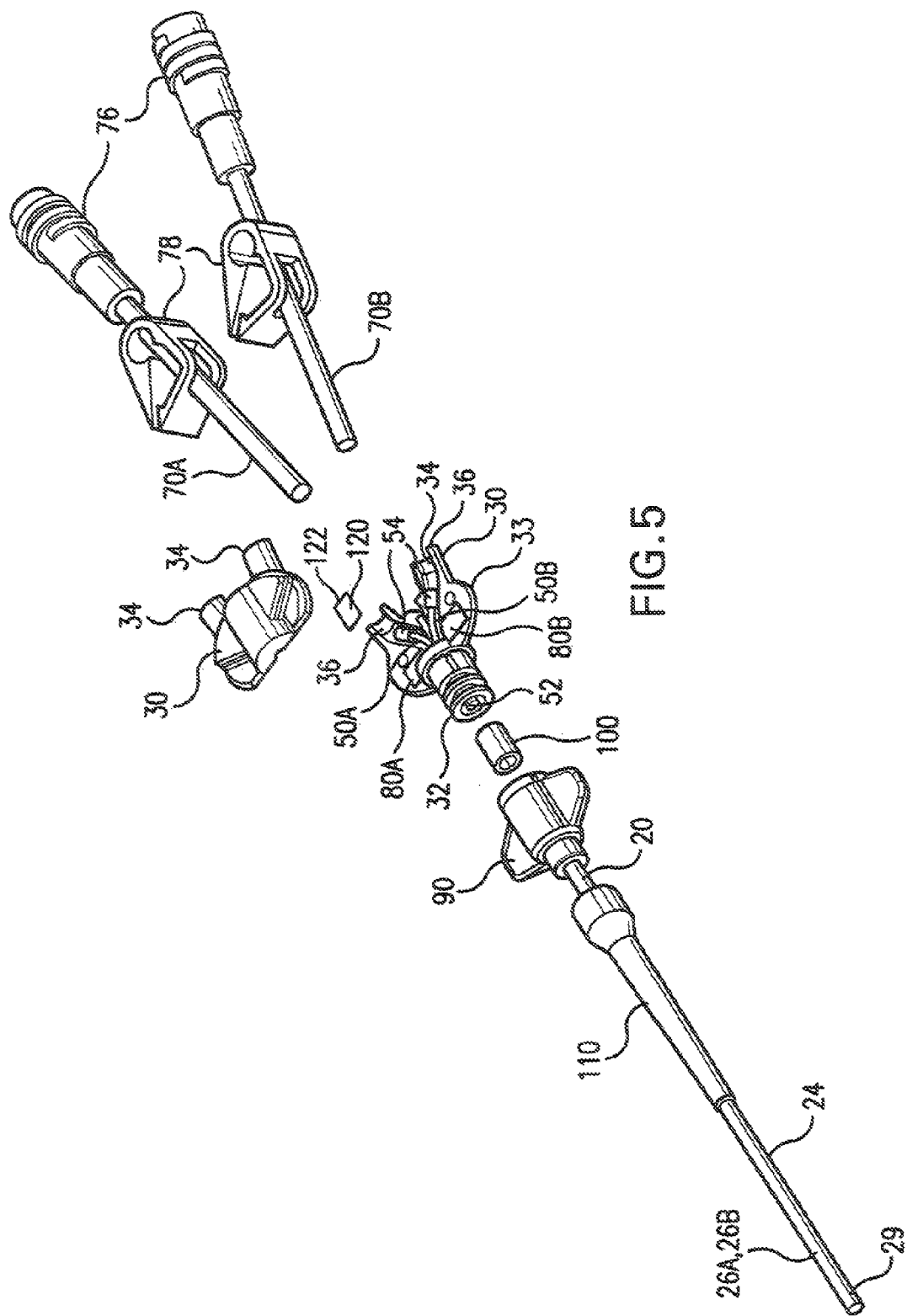
FIG. 5 is a partial perspective exploded view of a dual lumen catheter of the present invention.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "lumen" includes aspects having two or more such lumens unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The present invention may be understood more readily by reference to the following detailed description of preferred embodiments of the invention and the examples included therein and to the Figures and their previous and following description.

As used in the specification and the appended claims, by a "subject" or "patient" is meant an individual. The term does not denote a particular age or sex. In one aspect, the subject is a mammal such as a primate, including a human. The term includes human and veterinary subjects.

The terms "distal" and "proximal" refer, respectively, to the directions "away from" and "closer to" a practitioner inserting or repairing the catheter of a patient. The terminology includes the words above specifically mentioned, derivatives thereof, and words of similar import.

Referring to FIGS. 1-5, a first embodiment of an implantable catheter of the present invention is illustrated. As shown in FIG. 1, the catheter 10 comprises a single-lumen catheter tube 20, a means for trimming the catheter tube, a hub member 30, and an attachment tube 50. The catheter tube 20 has a distal end 22 and a tip 24. In one aspect, at least a portion of the catheter tube comprises a radiopaque material that is formed thereon the catheter tube through means currently known in the art. In one exemplary aspect, a stripe of radiopaque material is formed on the catheter tube proximate the tip 24 of the catheter tube 20. In another exemplary aspect, at least a portion of the tip of the catheter tube is formed of the radiopaque material. One would appreciate that it is contemplated that the radiopaque material can be formed in any desired geometric shape on any portion of the catheter tube proximate to or at the tip of the catheter tube.

The hub member 30 comprises a proximal port 32 and a distal port 34 and is configured such that the attachment tube 50 is mounted therein at least a portion of the hub member 30. In one aspect, the hub member 30 comprises at least one planer section 33 defining at least one opening 35 that can be used to suture the catheter to the patient to maintain the position of the catheter after insertion into the patient.

In one aspect, the attachment tube 50 has a first end 52 and opposed second end 54 and is configured to extend substantially therebetween portions of the proximal and distal ports of the hub member 30. In one example, portions of the hub member are formed axially around portions of the first and second ends of the attachment tube. In operation, the distal end 54 of the single lumen catheter tube 20 is configured to fit axially about an exterior surface 56 of the attachment tube. In one aspect, the cross-sectional shape of the single lumen 26 of the exemplified catheter tube. 20 has a complementary shape to the cross-sectional shape of the first end of the attachment tube. For example, and not meant to be limiting, the lumen 26 of the single-lumen catheter tube 20 and the first end 52 of the attachment tube 50 has a generally O-shaped cross-section. In another aspect, the attachment tube 50 can be made from, for example and not meant to be limiting, a biocompatible material such as titanium or stainless steel.

The catheter 10 further comprises an extension tube 70 that is connected to the second end 54 of the attachment tube. The extension tube 70 has a proximal portion 72 and a distal portion 74 and is in fluid communication with the single lumen 26 of the catheter tube through appropriate connection of the respective catheter and extension tubes to the attachment tube.

While FIGS. 1-4 illustrate the use of one attachment tube 50 and one extension tube 70 in fluid communication with the single lumen catheter tube 20, it is contemplated, as shown in FIG. 5, that a pair of attachment tubes 50A, 50B can be selectively coupled to a pair of extension tubes 70A, 70B and a dual lumen catheter tube 20. Of course, any appropriate configuration and number of attachment tubes, catheter lumens, and extension tubes should be considered within the scope of the invention.

For example, and referring to FIG. 5, for a dual lumen catheter, the catheter tube 20 comprises a pair of opposing lumens 26A, 26B that each has a generally D-shaped cross-section. In one exemplary aspect, a longitudinally extending septum may define each lumen 26 up through the distal end of the catheter tube. In this example, the catheter 10 comprises two attachment tubes 50A, 50B that are in fluid communication with two respective extension tubes 70A, 70B. In one exemplary aspect, the first end 52 of each attachment tube has a generally D-shaped cross-section complementary to the shape of each lumen 26A, 26B of the dual lumen catheter tube. In another aspect, the second end 54 of each attachment tube has a generally O-shaped cross-section that is complementary to the conventional round cross sectional shape of the extension tube 70A, 70B.

Of course, in reference to FIGS. 1-5, the first embodiment of the invention is described with preferred single and double lumen embodiments of the catheter, which comprise one attachment tube, a single lumen catheter tube, and one extension tube or, alternatively, a pair of attachment tubes, a dual lumen catheter tube, and a pair of extension tubes. The present invention should not be limited, however, to these preferred embodiments and other appropriate configurations should be considered within the scope of the invention. For example, the catheter may have any desired number of lumens that are similarly configured to communicate with the desired number of extension tubes.

In another aspect, the extension tube 70 can have a connector 76 that is securely attached to the distal portion 74 of the extension tube. In one example, the connector 76 can be a luer fitting, as known in the art. The connector 76 is configured to be attachable to a fluid conveying device or a medical device (not shown), as is known in the art. In a further aspect, each extension tube 70 comprises a clamp 78 for selectively clamping the extension tube when the catheter 10 is not connected to a fluid conveying device.

In one aspect, the distal end 22 of the catheter tube is trimmed to form a trimmed end portion 22' after the subcutaneous insertion of a portion of the catheter tube such that the tip 24 of the catheter tube is positioned into the desired anatomical position within the patient. The length of the catheter tube from the tip 24 to the trimmed end portion 22' is generally the desired length of the catheter tube. In one aspect, the catheter comprises a first cutting assembly 80 that is mounted therein an interior portion of the hub member intermediate the proximal and distal ports of the hub. In one aspect, the first cutting assembly 80 is connected to a portion of the exterior surface of the attachment tube 50. In a further aspect, the first cutting assembly 80 is configured to cut the lumen 26 of the catheter tube 20 as the catheter tube is forcefully drawn or pushed over and across the attachment tube and past the first cutting assembly. The generated "split" or waste catheter tube 28 is subsequently ejected from a conduit 36 defined therein the hub member 30. In one aspect, the conduit 36 extends between the first cutting assembly 80 and an exterior surface 38 of the hub member. In one exemplary aspect, the first cutting assembly 80 is a generally planer blade 82, such as, for example a razor blade, having at least one sharp edge 84. In another aspect, the first cutting assembly 80 is positioned substantially co-planer to the longitudinal axis of the portion of the attachment tube to which the first cutting assembly is connected. In this aspect, it is contemplated that the at least one sharp edge 84 is oriented toward the first end 52 of the attachment tube.

Alternatively, in the dual lumen catheter embodiment shown in FIG. 5, the first cutting assembly 80 comprises a pair of first cutting assemblies 80A, 80B that are mounted to the respective portions of the two attachment tubes 50A, 50B. In one aspect, the pair of first cutting assemblies is positioned such that they oppose each other. In another aspect, the pair of first cutting assemblies 80A, 80B is mounted within the hub member such that they are substantially co-planer.

In another aspect, the catheter 10 comprises a means for selectively positioning each respective lumen 26 of the trimmed end portion 22' of the catheter tube 20 into fluid communication with the respective first end 52 of the attachment tube. In one aspect, as noted above, the connection between the lumen 26 of the catheter tube and the first end 52 of the attachment tube is an overlapping fixed connection. However, any other appropriate fastening means, such as detents, barbs, and the like, may be used.

In one aspect, the catheter 10 comprises a twist locking cap 90 that is configured to fit axially about the exterior surface 29 of the catheter tube. In one aspect, the locking cap 90 is also configured for slideable movement along the exterior surface of the catheter tube and for selective connection to the proximal port 32 of the hub member 30. The twist locking cap 90 has an interior surface that is sized and shaped to rotatably mount to a complimentarily shaped surface on the proximal port of the hub. In one aspect, the proximal port 32 of the hub member is externally threaded and the locking cap is complimentarily internally threaded. Thus, it is contemplated that the locking cap 90 and the hub member 30 be appropriately threaded such that the locking cap 90 is selectively attachable to the threaded portion of the proximal port 32 of the hub member such that the catheter tube is securely attached to the hub member.

In one aspect, the catheter further comprises a gasket sleeve 100 that is configured to fit axially about the exterior surface 29 of the catheter tube 20 as well as axially about the first end portion of the attachment tube 50. In one exemplary aspect, the gasket sleeve 100 can be made from an at least partially malleable material so as to provide further compression about the connection between the lumen of the catheter tube and the attachment tube. In another aspect, the gasket sleeve 100 is formed from a non-malleable material. In one exemplary aspect, after the hub member 30 is selectively positioned with respect to the catheter tube 20, a fluid tight seal between the lumen 26 of the catheter tube and the attachment tube 50 is formed by forcefully sliding the gasket sleeve 90 over the portions of the lumen 26 that are mounted thereon the first end 52 of the attachment tube. The act of forcefully sliding the gasket sleeve 100 over the lumen 26 of the catheter tube 20 compresses the connection between the lumen and attachment tube to form a secure, fluid tight seal.

In a further aspect, and as shown in FIG. 4, the locking cap 90 comprises an interior axial shoulder surface 92 that is configured to engage an end of the gasket sleeve 100. Thus, in operation when the locking cap 90 is selectively secured onto the proximal port 32 of the hub member, the anterior axial shoulder surface 92 acts on an end of the gasket sleeve 100 to provide the desired force to forcefully push the gasket sleeve 100 into the desired compressive relationship with the lumen.

In another aspect, the catheter comprises a hemostasis taper sleeve 110 that is configured to fit axially about the exterior surface of the catheter tube and for slideable movement along the exterior surface of the catheter tube. In another aspect, an end portion 112 of the hemostasis taper sleeve 110 is configured for rotatably mounting thereon a bottom portion 94 of the locking cap 90.

In another aspect, the catheter 10 can also comprise a waste cutting assembly 120 that is mountable thereon the hub member 30 for selective cutting off of a portion of the exposed waste catheter tube 28. As one will appreciate at least one edge of the waste cutting assembly is a sharp edge 122. Thus, as one skilled in the art will appreciate, as the waste lumen 28 is ejected from the hub member through the conduit, it can be drawn down to engage the waste cutting assembly for trimming and removal of the waste lumen. Alternatively, it is contemplated that the waste catheter tube 28 could be removed through conventional cutting means, such as, for example and not meant to be limiting, scissors, blades, scalpels, and the like.

In use, the patient is prepped for the introduction of the catheter 10 by conventional methodologies. An incision is made near the area to be catheterized and the tip of the catheter is introduced into a selected vessel of the patient such that the tip of the catheter tube is routed to and positioned in the patient's body at the desired anatomical location. The hub member is drawn down the portion of the catheter tube that is exposed exterior to the surface of the incision site toward its desired position, which forces portions of the lumen of the catheter tube to be drawn past the first cutting assembly and cut. Thus, the catheter tube is trimmed to a desired length. In one aspect, and as noted above, the split or waste lumen is ejected from the conduit of the hub member as the hub member is drawn down the catheter tube and into its desired position. Finally, a fluid tight connection between the lumen of the trimmed end portion of the catheter tube and the attachment tube is created.

Referring now to FIG. 5, a dual lumen catheter of the present embodiment of the catheter is shown. As previously discussed, the illustrated catheter comprises: a hub member 30 having a proximal port and a distal port; a pair of attachment tubes 50A, 50B mounted therein the hub member and extending substantially therebetween the proximal and distal ports of the hub member; a dual lumen catheter tube 20 that is mountable thereon a portion of the attachment tubes the proximal port of the hub; and a pair of extension tubes 70A, 70B connected to the portions of the attachment tubes proximate the distal port of the hub. The catheter further comprises a pair of first cutting assemblies 80A, 80B mounted therein an interior portion of the hub member, intermediate the proximal and distal ports of the hub, that are configured to cut the lumen 26 of the catheter tube 20 as it is drawn past the cutting assemblies.

As described above, the catheter 10 also comprises a twist locking cap 90 that is constructed and arranged for, mounting thereon the end portion 112 of the hemostasis taper sleeve. The twist locking cap 90 is threaded to selectively engage the complimentarily threaded surface on the proximal port 32 of the hub. In one aspect, the catheter 10 can further comprise a cylindrical gasket sleeve 100 that is positioned therebetween the twist locking cap 90 and the proximal port 32 of the hub member. In a further aspect, the gasket sleeve 100 is configured to be forced into an engaged position with the respective lumens 26A, 26B of the dual lumen catheter tube when the locking cap 90 is twisted onto the proximal port 32 of the hub member such that a fluid tight connection is created between each respective lumen 26 and the respective first end 52 of the attachment tubes 50A, 50B.

Figure 6:
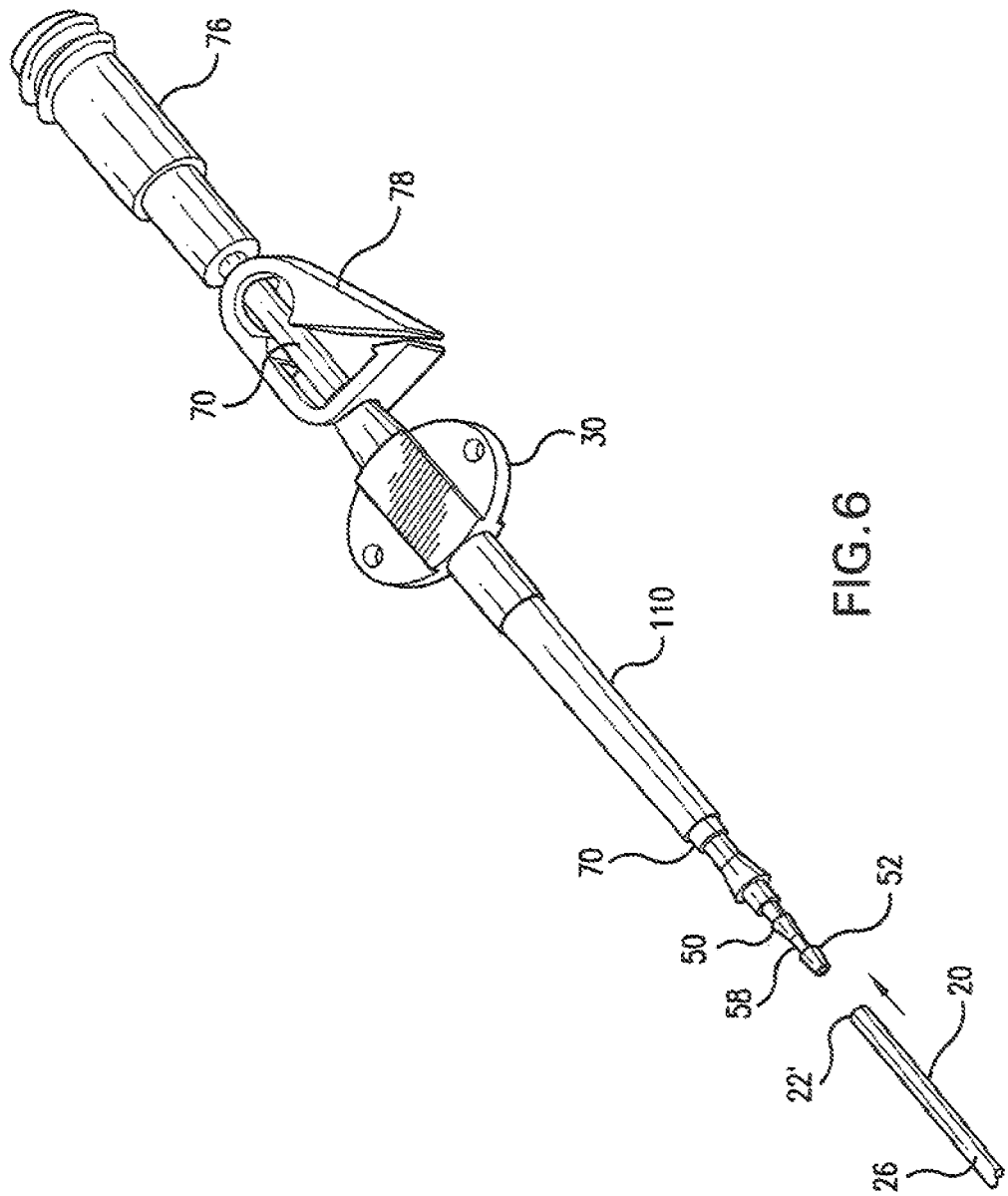
FIG. 6 is a partial perspective view of a second embodiment of the catheter of the present invention for a single lumen catheter, showing the hub member of the catheter being connected to the trimmed end of the inserted catheter, and showing the attachment tube having a first end portion that has a barbed exterior surface portion, an intermediate portion that has a raised shoulder surface, and a second end portion adapted to connect to an extension tube.
Figure 7:
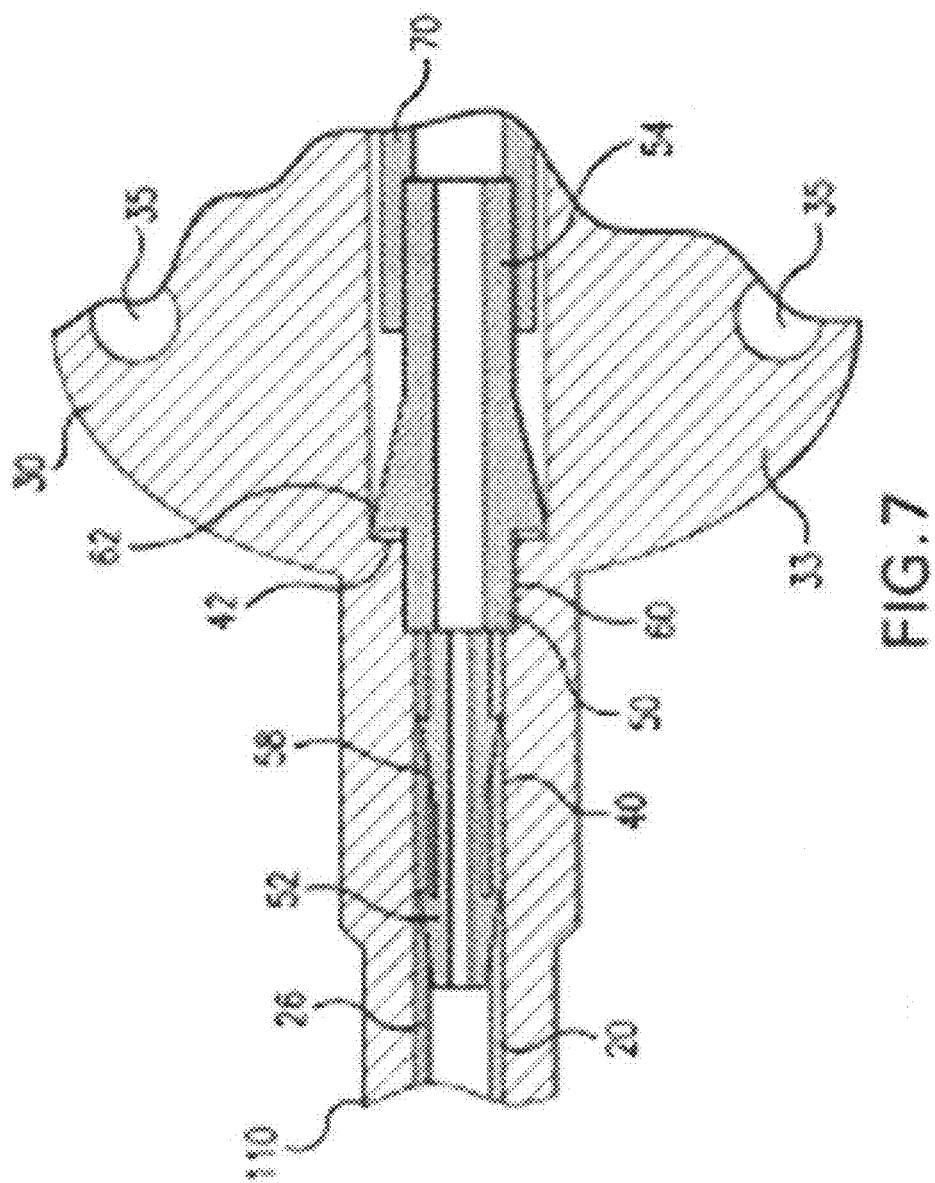
FIG. 7 shows a partial cross-sectional view of the catheter of FIG. 6, showing a raised shoulder member being position into locking engagement with a complimentarily shoulder surface defined therein the hub member.
Figure 8:
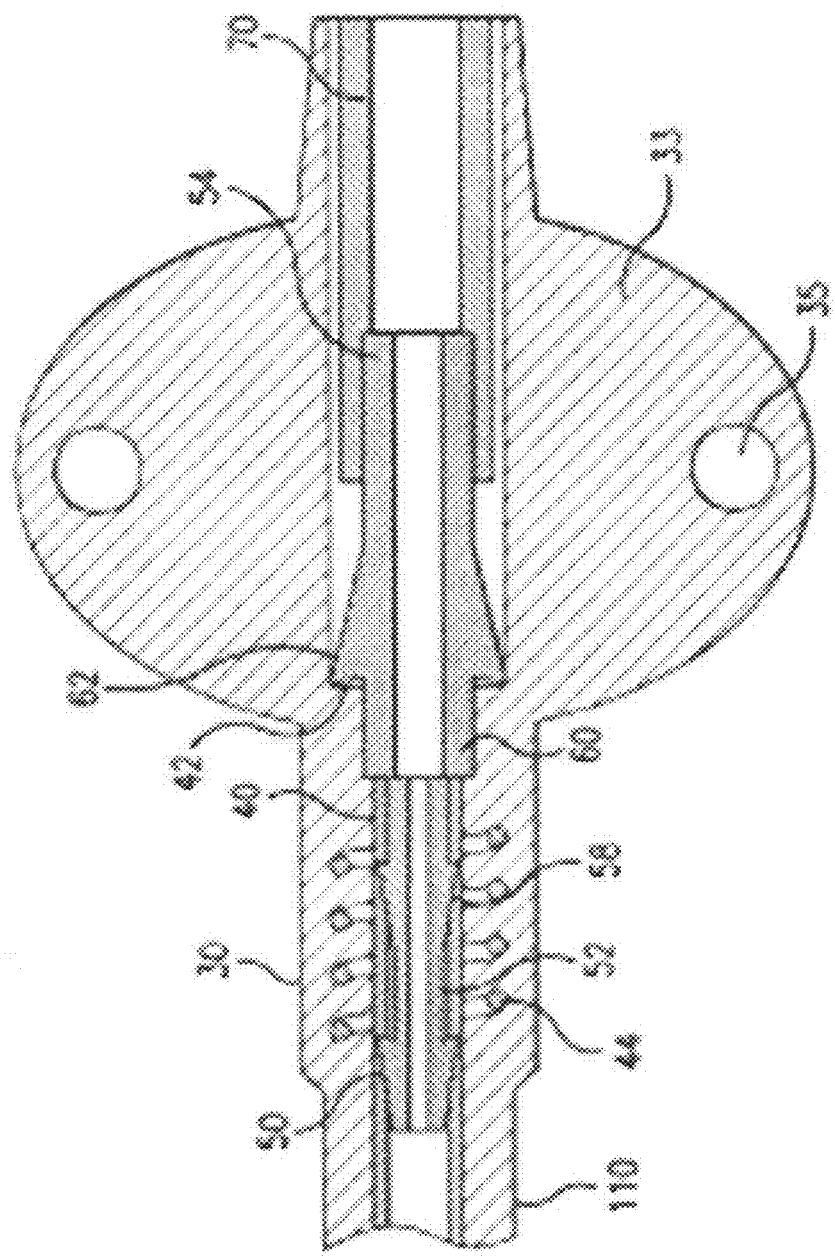
FIG. 8 shows a partial cross-sectional view of the raised shoulder member being position into locking engagement with a complimentarily shoulder surface defined therein the hub member and showing a spring mounted therein a portion of the hub member.

FIGS. 6-8 illustrate a second embodiment of the catheter 10 of the present invention. In this aspect, the attachment tube 50 of the catheter assembly has a first end portion 52 that has a barbed exterior surface portion forming a barbed connector 58, an intermediate portion 60 that has a raised shoulder member 62, and a second end portion 54 adapted to connect to an extension tube 70. Here, the end of the single lumen catheter tube 20 is connected to the first end portion 52 of the attachment tube after being trimmed to a desired length via cutting means known in the art. As one will appreciate, the barbed connector 58 at the first end portion of the attachment tube provides for internal sealing between the attachment tube 50 and the single lumen catheter 20. The attachment tube, with the trimmed end of the catheter tube mounted thereon, is then drawn up a conduit 40 defined within a portion of the hub member 30 until the raised shoulder member 62 of the attachment tube is positioned into a locking engagement position with a complementary shoulder surface 42 defined therein the conduit 40 of the hub member to secure the attachment tube relative to the hub member. In one aspect, at least a portion of the hub member through which the conduit passes forms the hemostasis taper sleeve 110. In operation, it is contemplated that, depending on the length of the trimmed end of the catheter with respect to the incision site, at least a portion of the hemostasis taper sleeve is positioned subcutaneously.

In a further aspect, the attachment tube 50 is connected to a rod that can be drawn to pull the attachment tube into the locking engagement position. In still another aspect, the hub member 30 can comprise a spring element 44 that is positioned to axially surround a portion of the conduit proximal the complementary shoulder surface defined therein the conduit of the hub member so that a compressive force can be applied to the lumen of the catheter tube to force the lumen 26 into a secure attachment with the underlying first end portion of the attachment tube 50.

Referring now to FIGS. 9-11, a third embodiment of a dual lumen catheter of the present invention is illustrated. In this aspect, the dual lumen catheter tube 20 is connected to respective attachment tubes 50A, 50B of a pair of attachment tubes after trimming to the desired length. The pair of attachment tubes are mounted at least partially therein the hub member 30 of the catheter. In one aspect, the first ends 52 of the attachment tubes have a D-shaped cross-section and are positioned in opposition. In another aspect, portions of the first ends 52 of the attachment tubes have peripherally extending barb portions 58. In one aspect, the barbed portions of the pair of attachment tubes are shaped and positioned to form staggered double barbed portions. As one would appreciate, the extension legs are positioned in fluid communication with the attachment tubes.

In this aspect, the catheter 10 comprises a hemostasis taper sleeve 110 that is axially and slideably mounted thereon a portion of the dual lumen catheter and a snap fit locking cap 90 mounted thereon the end portion of the hemostasis taper sleeve. As shown in FIG. 11, the snap fit locking cap 90 and a portion of the proximal port 32 of the hub member 20 are configured to form a snap fit as the locking cap is forced onto the proximal port of the hub into a connected position. In use, the trimmed ends 22' of the D-shaped lumens 26A, 26B of the dual lumen catheter tube are mounted thereon the barbed portion 58 of the attachment tubes and then the snap fit cap is moved from a disconnected position to a connected position to compressively secure the hub member to the catheter tube of the catheter.

A fourth embodiment of the implantable catheter 10 of the present invention is illustrated in FIGS. 12-14B. In this aspect, the catheter comprises a dual lumen catheter tube 20 and a hub member 30 within which a pair of attachment tubes 50A, 50B are mounted. As will be appreciated by one skilled in the art, each attachment tube is in fluid communication with one respective lumen 26 of the dual lumen catheter tube 20. The catheter further comprises a pair of extension legs 70A, 70B that in fluid communication with the pair of attachment tubes. The extension legs are configured for conventional connection to medical devices. The catheter also comprises a hemostasis tapered sleeve 110 mounted thereon an exterior surface 29 of the dual lumen catheter tube. In operation, the catheter 10 allows a conduit to be formed between the distal end 74 of the extension legs, a lumen 26 of the dual lumen catheter, and the patient's internal fluid pathways.

In this embodiment of the catheter 10, the trimmed ends 22' of the lumens of the dual lumen catheter tube 20 are attached to the first ends 52 of the attachment tubes after the dual lumen catheter tube is positioned proximate it desired location and after the distal end 22, opposite to its radiopaque tip 24, of the dual lumen catheter is trimmed to its desired length. In another aspect, the catheter comprises a compression ring fitting 140 that is axially mounted to the dual lumen catheter tube 20 proximate the hemostasis taper sleeve 110 and a locking cap 142, such as an anti-slip nut, that is axially mounted to the dual lumen catheter tube intermediate the hemostasis taper sleeve 110 and the compression ring fitting 140.

Figure 14B:
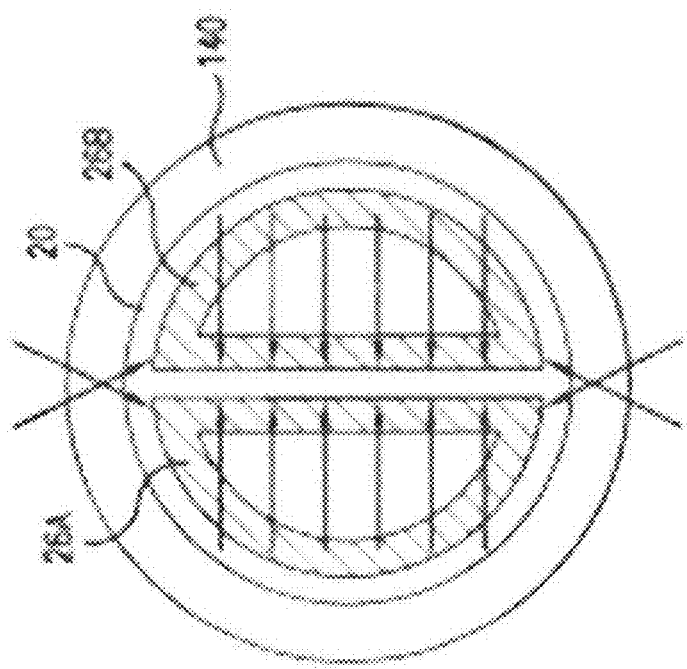
FIGS. 14A and 14B are cross-sectional end views of the D-shaped attachment tubes of FIG. 13.
Figure 14A:
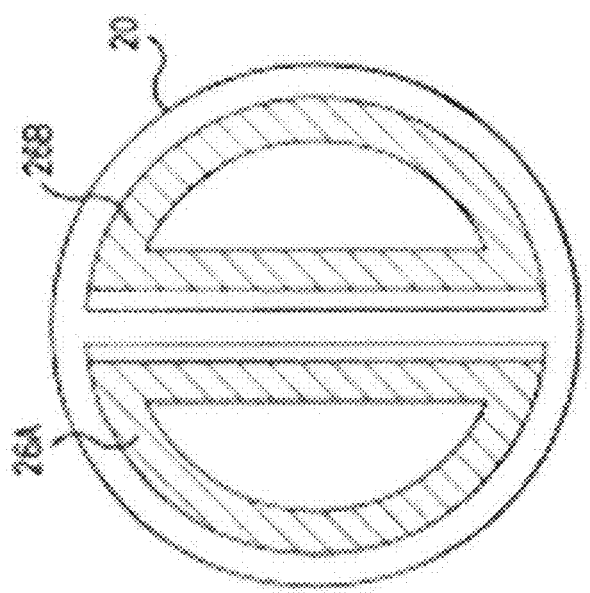

As one will appreciate, and as shown in FIGS. 14A and 14B, the seal between the dual lumen catheter tube and the attachment tubes is generated by attaching the compression ring fitting 140 to the proximal port 32 of the hub member by turning the ring fitting so that the female treaded portion of the ring fitting received the male treaded portion of the proximal port 32 of the hub member. This forces the compression ring fitting 140 over into an axial overlying position about the trimmed end portion of the catheter tube 20 and the attachment tubes and into a compressive relationship such that a secure fluid tight connection between with the catheter tube and the attachment tubes is formed. In this aspect, at least the first end 52 of the attachment tubes has a D-shape cross section. For example, the compression ring fitting 140 can be made of metal or plastic.

Figure 17:
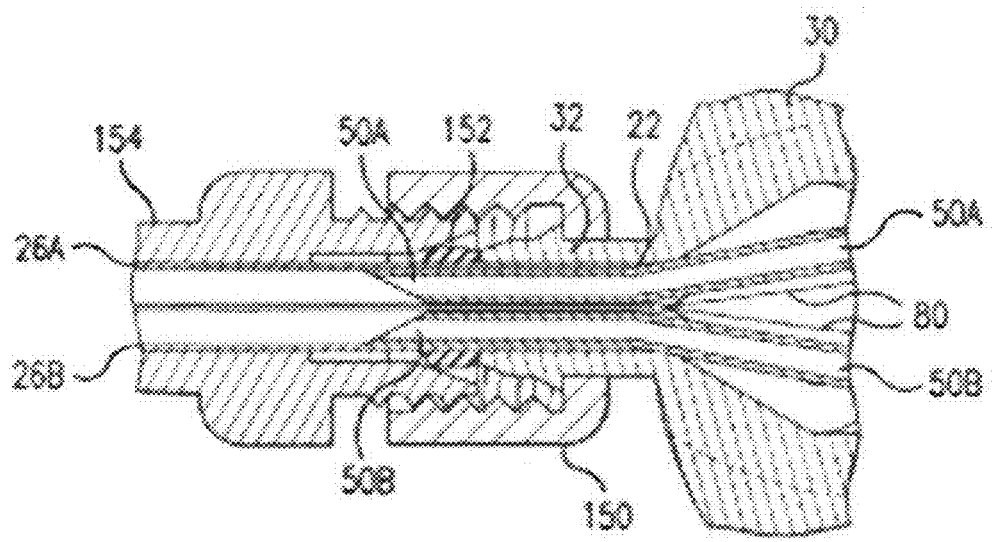
FIG. 17 is a cross-sectional view of a portion of the catheter showing the clamping cap positioned thereon on the proximal port of the hub member such that the compression ring fitting does not preclude drawing the waste portion of the dual lumen catheter through and out of the outlet of the hub member.
Figure 18:
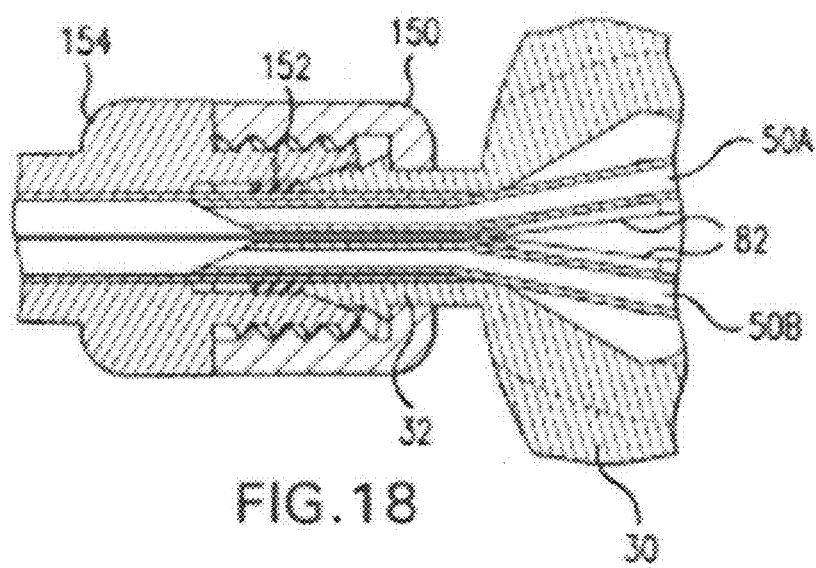
FIG. 18 is a cross-section view of the catheter showing the clamping cap positioned thereon the proximal port of the hub and engaged thereto the hemostasis taper sleeve such that the compression ring fitting is forced into operative cooperation with the hub member.

Turning to FIGS. 15-18, a fifth embodiment of the catheter 10 of the present invention is illustrated. In one aspect, the hub member 30 of the exemplified catheter comprises an embedded cutting assembly 80, such as, for example, a razor blade, that is constructed and arranged to cut the excess or waste catheter lumen as it is selectively drawn through the hub member. This allows for the catheter tube 20 to be selectively trimmed to a desired length. The catheter of this aspect also comprises a clamping cap 150, a compression ring 152, and a threaded hemostasis taper sleeve 154 that is, as shown in FIGS. 17 and 18, configured to generate compression onto the compression ring when the hemostasis taper sleeve is threadably engaged to the clamping cap. In this aspect, the clamping cap is mounted directly to the proximal port 32 of the hub member. In operation, the excess or waste catheter tube 28 is drawn through an outlet 156 in the hub member and is trimmed off. In another aspect, the hub member 30 can include a hinged door 158, which is positioned in a closed position over the outlet after the waste lumen is trimmed off and after engagement of the catheter tube and the attachment tubes mounted at least partially therein the hub member.

In this aspect, the compression ring 152, which can, for example, be made from plastic or metal, is mounted axially thereon a portion of the dual lumen catheter tube 20 proximate to the hemostasis taper sleeve 154. Further, in this aspect, the catheter lumens 26A, 26B are pre-attached to the attachment tubes 50 mounted therein the hub member. As one will appreciate, the length of the catheter lumen 26 is trimmed via the embedded cutting assembly 80 in the hub member that cuts the catheter tube as the catheter tube is pushed or drawn past the cutting assembly 80 in a sliding motion. As one will appreciate, the cutting assembly 80 is positioned distal to the first end 52 of the attachment tubes. The waste catheter is trimmed, and the hub member 30 is secured in fixed relationship to the sized catheter lumen via the above referenced compression of the compression ring 152 such that a secure fluid tight connection between the lumens of the catheter tube and the attachment tubes mounted therein the hub member.

A sixth embodiment of the catheter 10 of the present invention is illustrated in FIGS. 19-21A. In this aspect, the catheter comprises a clamping collet assembly 160 that is constructed and arranged to provide a fluid tight seal between the lumens 26A, 26B of the dual lumen catheter tube 20 and the attachment tubes 50A, 50B mounted therein the hub member of the catheter. In one aspect, at least a portion of each of the first ends 52 of the attachment tubes has a D-shape cross-section. In this aspect, the clamping collet assembly 160 comprises a clamping nut 162 rotatably mounted on a clamping collet 164 that is formed on the proximal port 32 of the hub member that is configured to threadably cooperate with the clamping nut.

In use, the trimmed end portions 22' of the lumens of the catheter tube are attached to the attachment tubes after trimming the catheter tube 20 to the desired length. In this aspect, a portion of the hemostasis taper sleeve 166 is clamped therebetween the clamping collet 164 and the exterior of the catheter lumen to provide compression on the lumens 26A, 26B of the catheter tube and onto the underlying first ends 52 of the attachment tubes 50A, 50B when the clamping nut 162 is threadably engaged. In another aspect, the hemostasis plug and lumens of the catheter tubes are positioned with respect to the attachment tubes at the same time to the attachment tubes prior to engaging the collet assembly to secure the catheter tube relative to the attachment tubes.

Figure 22:
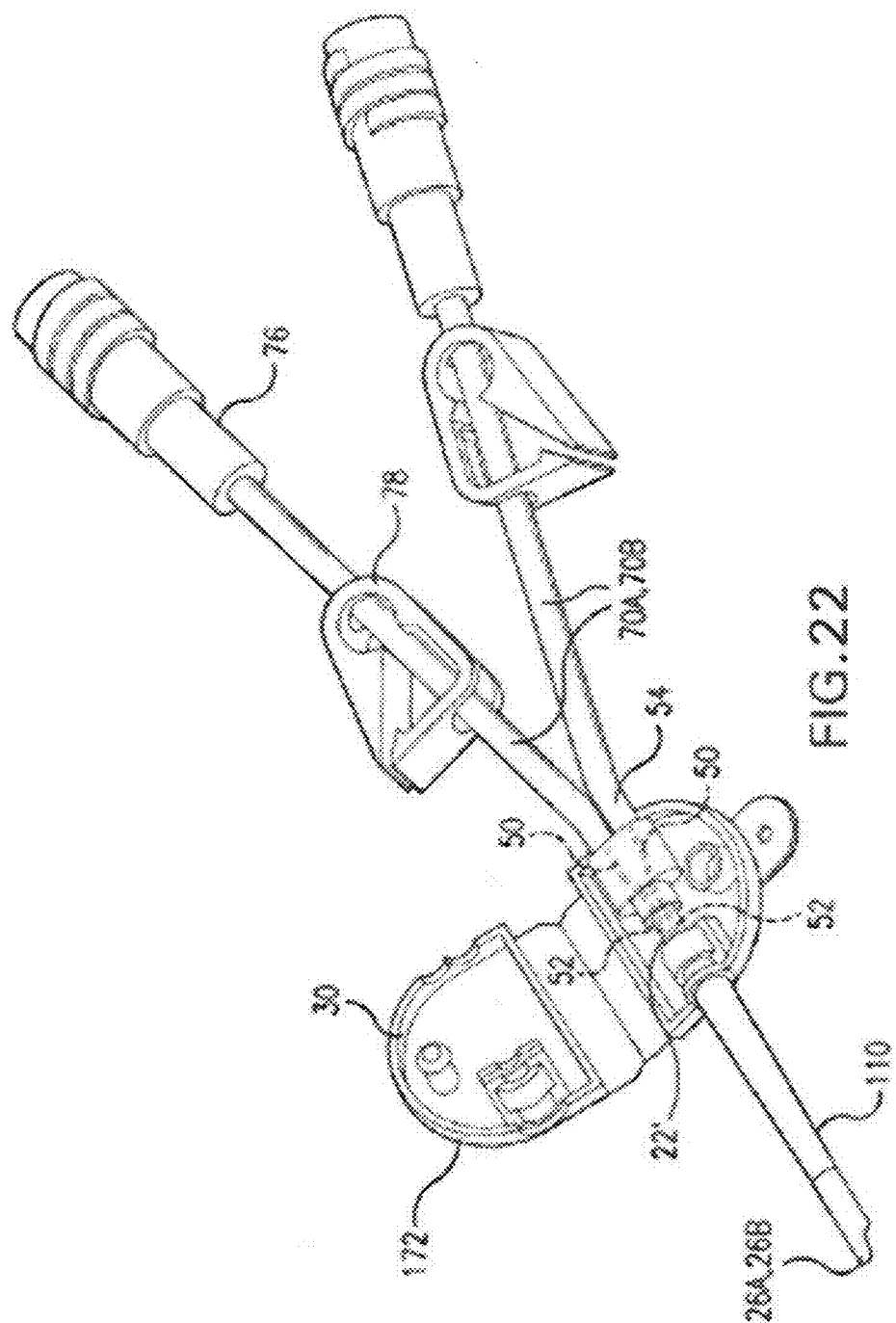
FIG. 22 is a partial perspective view of a seventh embodiment of the catheter of the present invention for a dual lumen catheter, showing a hub member selectively open and attachment tubes that are mountable therein the interior of the hub member.
Figure 23:
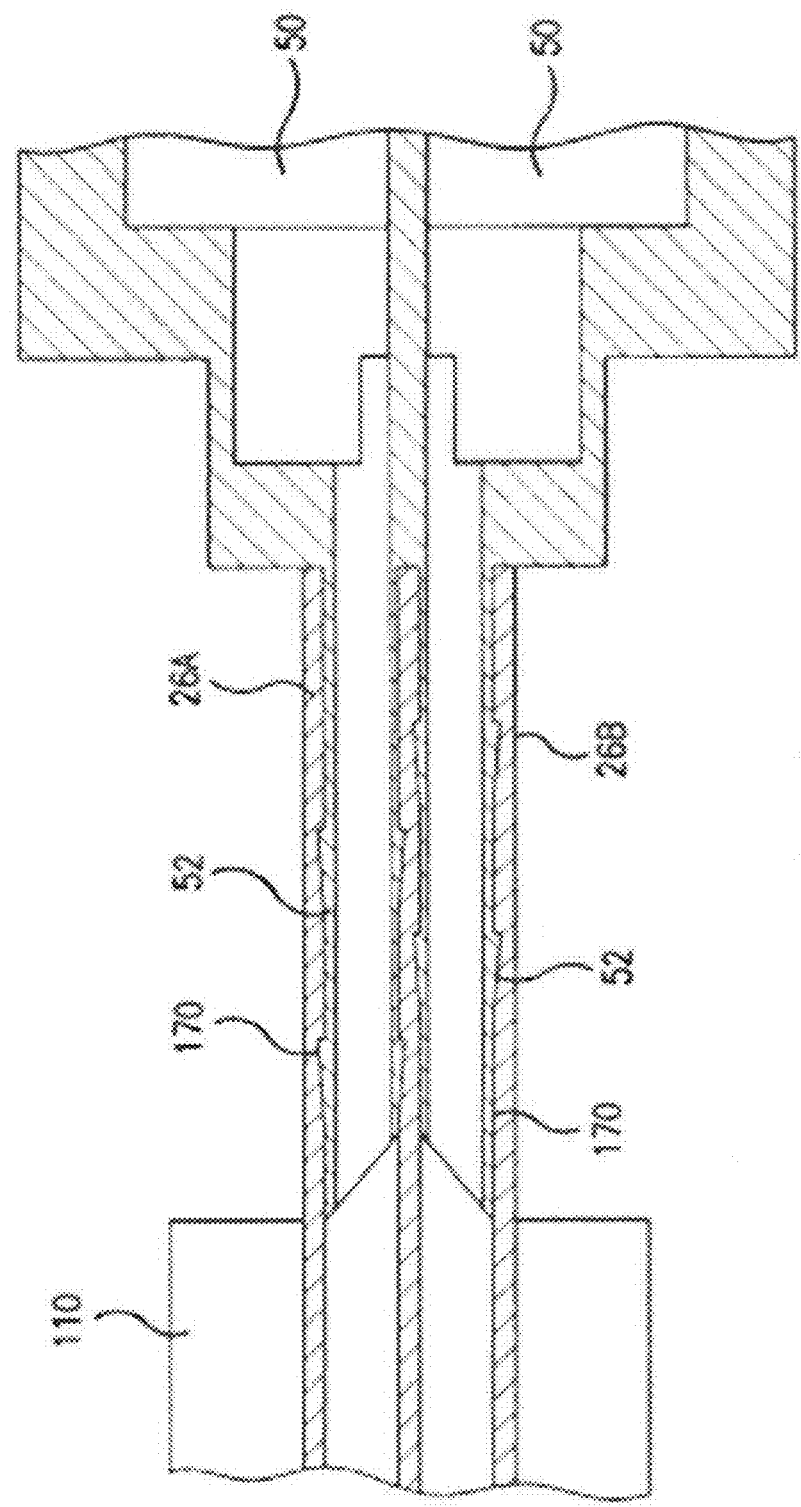
FIG. 23 is a partial cross-sectional view showing the catheter lumen mounted thereon the first end portions of the attachment tubes.

Turning to FIGS. 22 and 23, a seventh embodiment of the catheter 10 of the present invention comprises a hub member 30 having attachment tubes 50A, 50B mounted therein that are configured to connect to the trimmed end 22' of the catheter lumen. In one aspect, the attachment tubes 50 have a barbed surface portion 170 at a first end thereof. The extension legs 70 are connected to and in fluid communication with the second ends 54 of the attachment tubes. In one aspect, the attachment tubes 50 form a staggered double barbed mounting assembly that is adapted to mount the trimmed end portions of the lumens of the catheter tube thereto.

In this embodiment, the lumens 26A, 26B of the catheter tube are attached to the barbed surface portion 170 of the attachment tubes after trimming the catheter tube to the desired length. As one will appreciate, the barbed surface portion 170 generates internal interference between the catheter lumen 20 and the attachment tubes 50 and helps provides internal sealing.

In a further aspect, the hub member 30 comprises a snap fit hub housing 172 that is configured to mount therein a portion of the hemostasis taper sleeve and the attachment tubes. In use, a portion of the hemostasis taper sleeve, the attachment tubes, portions of the extension tube, as well as portions of the trimmed ends of the lumens of the catheter tube that are connected to the first ends of the attachment tubes are mounted therein respective portions of the housing and the housing is closed to secure the positions of the hemostasis taper sleeve, the attachment tubes, portions of the extension tube, as well as portions of the trimmed ends of the lumens of the catheter tube relative to each other. Thus, the snap fit housing provides additional sealing and security for the catheter assembly.

Figure 24:
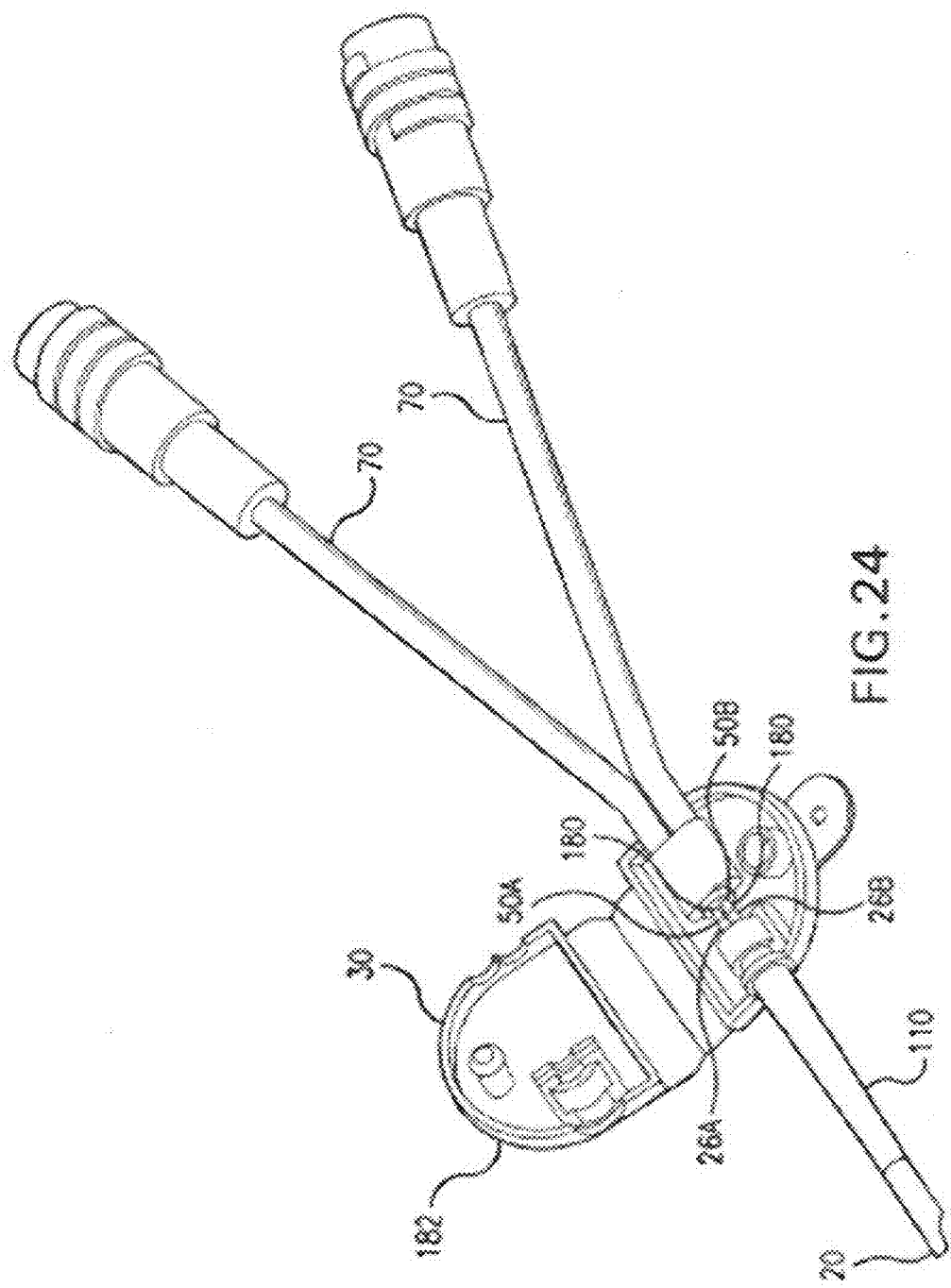
FIG. 24 is a partial perspective view of an eighth embodiment of the catheter of the present invention for a dual lumen catheter, showing a hub member selectively open and attachment tubes that are mountable therein the interior of the hub member.
Figure 25:
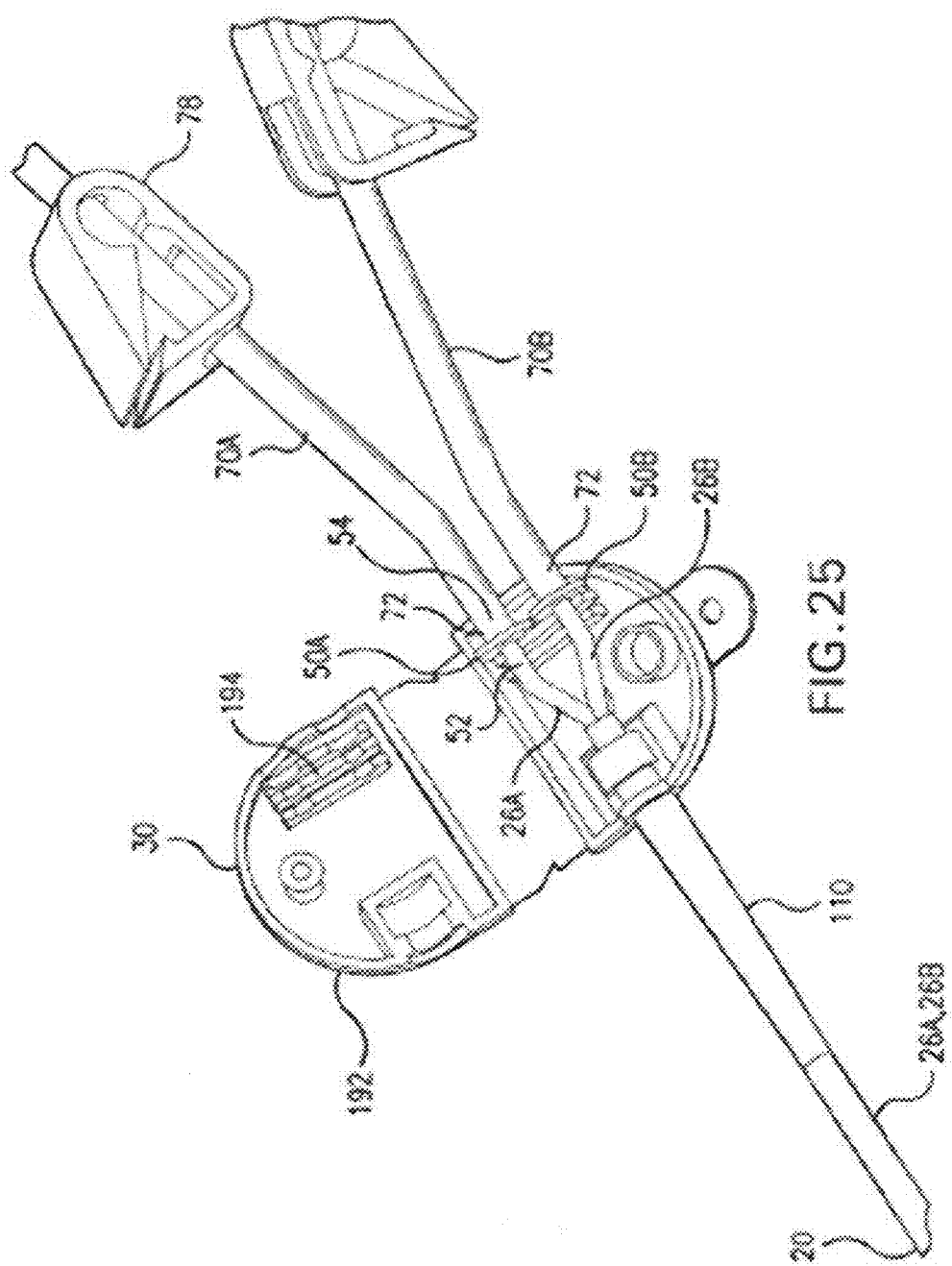
FIG. 25 is a partial perspective view of an ninth embodiment of the catheter of the present invention for a dual lumen catheter, showing a snap fit hub housing being connected to a portion of the hemostasis plug and the barb fittings to secure the hemostasis taper sleeve and the barb fittings of the attachment tubes relative to each other.

FIGS. 24-25 illustrate an eighth embodiment of the catheter 10 of the present invention. In this aspect, which is similar to the seventh embodiment described above, attachment tubes 50A, 50B are provided that are in fluid communication with the pair of extension tubes 70A, 70B. Each attachment leg has at least one barbed surface portion 180 and the respective attachment legs are positioned such that the at least one barbed surface portions are positioned co-planer to each other, i.e., in a side-by-side relationship.

In this aspect, the lumens 26A, 26B of the dual lumen catheter tube 20 are attached to the attachment tubes 50A, 50B after trimming of the catheter tube 20 to the desired length. The barbed surface portions 180 of the attachment tubes provide for internal sealing and a secure fit between the lumens of the catheter tube and the respective attachment tubes.

In a further aspect, the hub member 30 comprises a snap fit housing 182 that is configured to mount therein a portion of the hemostasis plug, portions of the extension tubes, the attachment tubes, as well as portions of the lumens of the catheter tube that are mounted thereon the first ends of the attachment tubes. In use, the snap fit housing is closed to secure the portions of the catheter that are mounted therein the interior of the snap fit housing relative to each other to provide additional sealing and security for the catheter.

Figure 26:
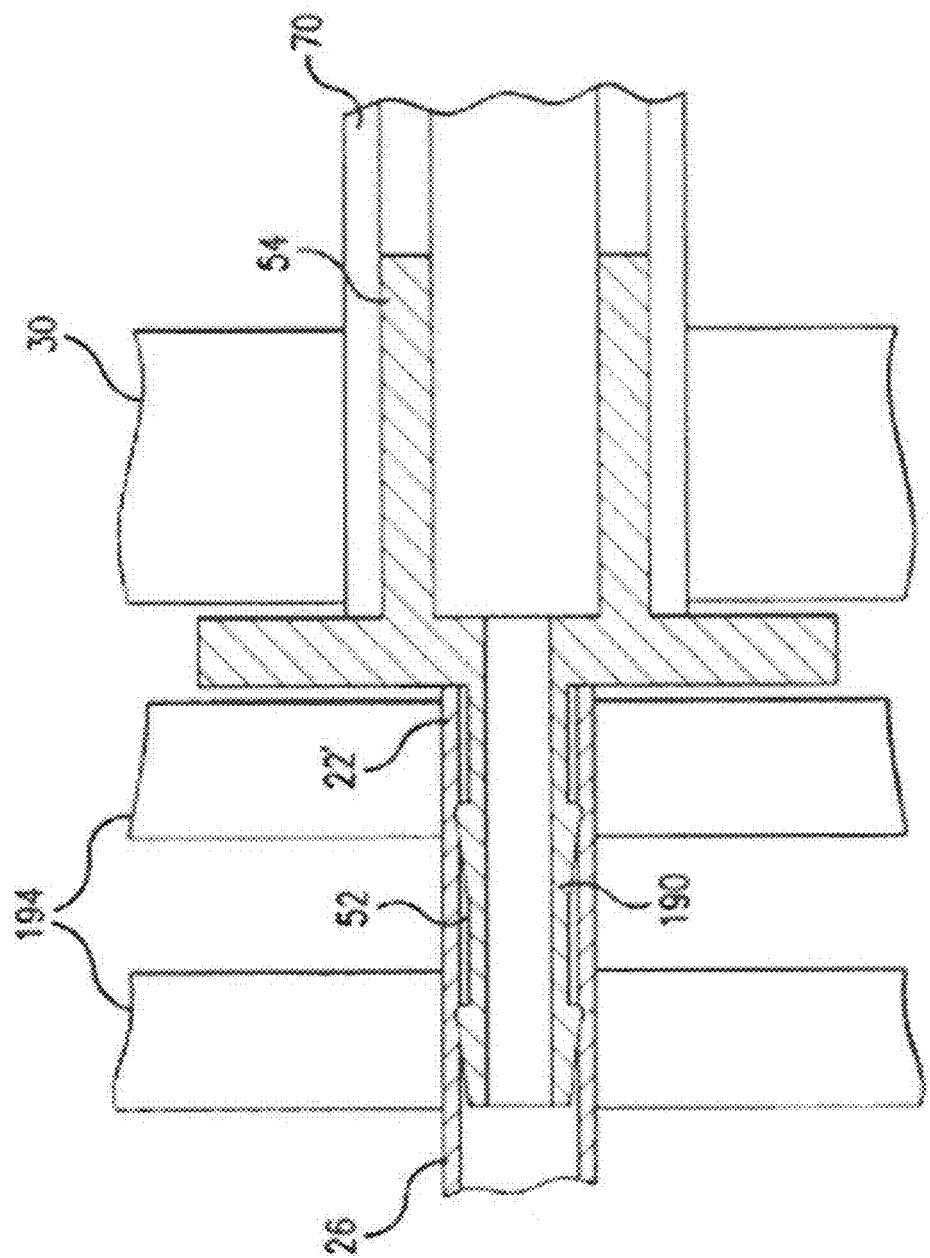
FIG. 26 is a partial cross-sectional view showing the catheter lumen and the extension tube mounted thereon the respective end portions of the barbed fitting of an attachment tube, and showing the barb fitting mounted therein a support member of the hub housing to relieve stress on the respective connections.
Figure 27:
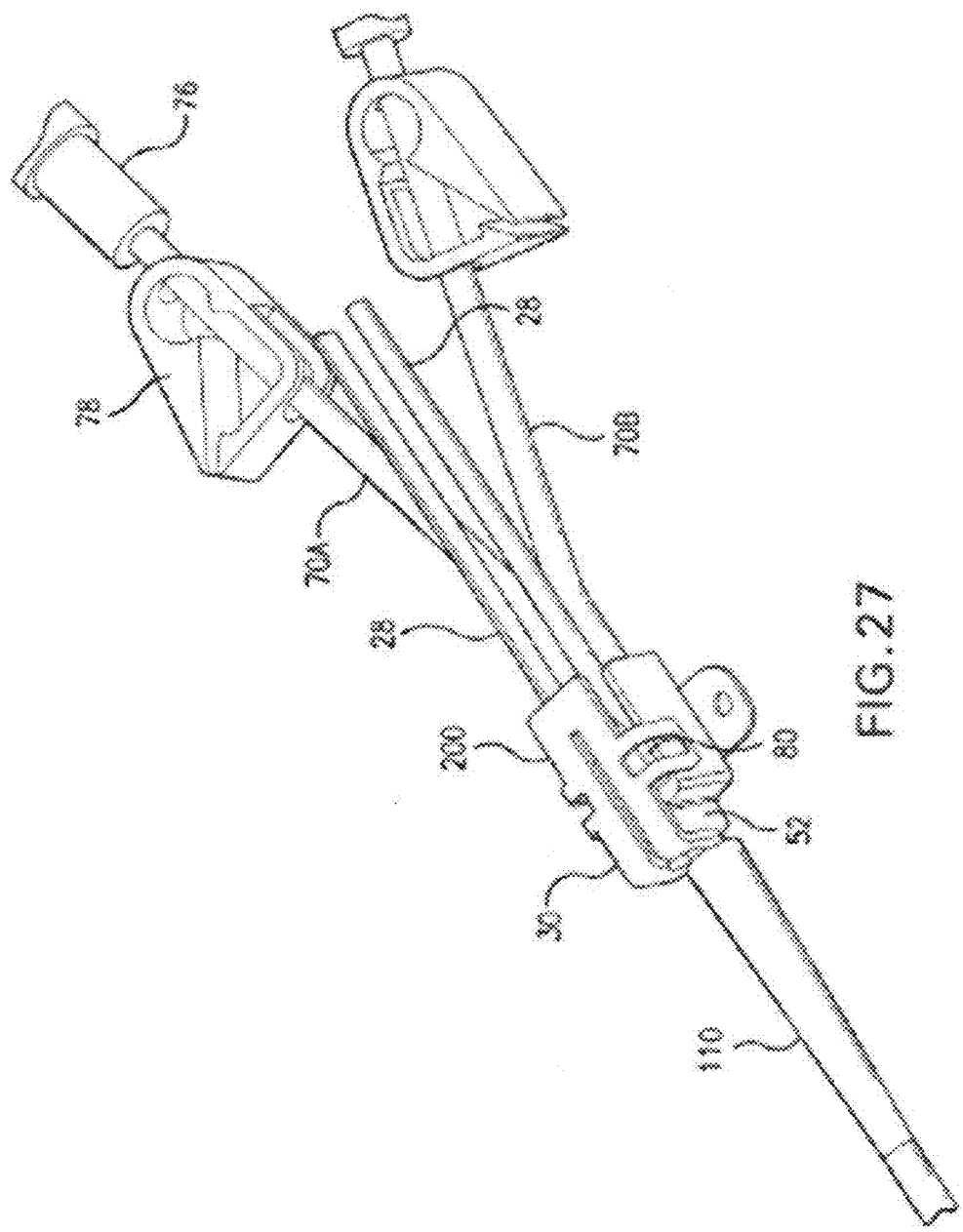
FIG. 27 is a partial perspective view of a tenth embodiment of the catheter of the present invention, showing a snap clip locking mechanism in an unlocked position.

A ninth embodiment of the present invention is shown in FIGS. 25-26. In this aspect, a catheter lumen trimming assembly is provided [not shown]. The catheter lumen trimming assembly is constructed and arranged to cut the outer sheath of a dual lumen catheter tube and to spread and separate the two internal lumens 26a, 26B of the dual lumen catheter as the catheter lumen is drawn through the catheter lumen trimming assembly. As shown in the figures, the dual lumen catheter is conventional and comprises two round single lumens 26A, 26B that are encapsulated inside an outer shield to form two D-shaped fluid pathways. The catheter also comprises a pair of barbed fittings 190 that that form a portion of the first ends 52 of the attachment tubes 50 of the catheter 10. The attachment tubes 50A, 50B are positioned in fluid communication with the extension tubes 70A, 70B.

In operation, each attachment tube is mounted therebetween the trimmed end of one respective formed single lumen and one respective extension tube. The barbed fittings 190 of the respective attachment tubes 50 are configured to securely grasp a portion of the trimmed end 22' of the respective formed single lumen 26. The hub member 30 of the catheter of this embodiment further comprises a snap fit hub housing 192 that is formed to allow for the mounting of a portion of the hemostasis taper sleeve and the barb fittings to secure the hemostasis taper sleeve and the barb fittings of the attachment tubes relative to each other.

In operation, the snap fit housing 192 is closed to secure the portion of the hemostasis plug and the barb fittings relative to each other and to provide additional sealing and security for the catheter. The housing comprises an internal support member 194 that is constructed and arranged to mount the barb fitting 190 therein such that stress is relieved on the respective connections between the single lumen catheter and the extension tube. In another aspect, and as shown in FIG. 26, the internal support structure member can assist in maintaining a compressive relationship between the barbed fitting and the formed single lumen.

Figure 28:
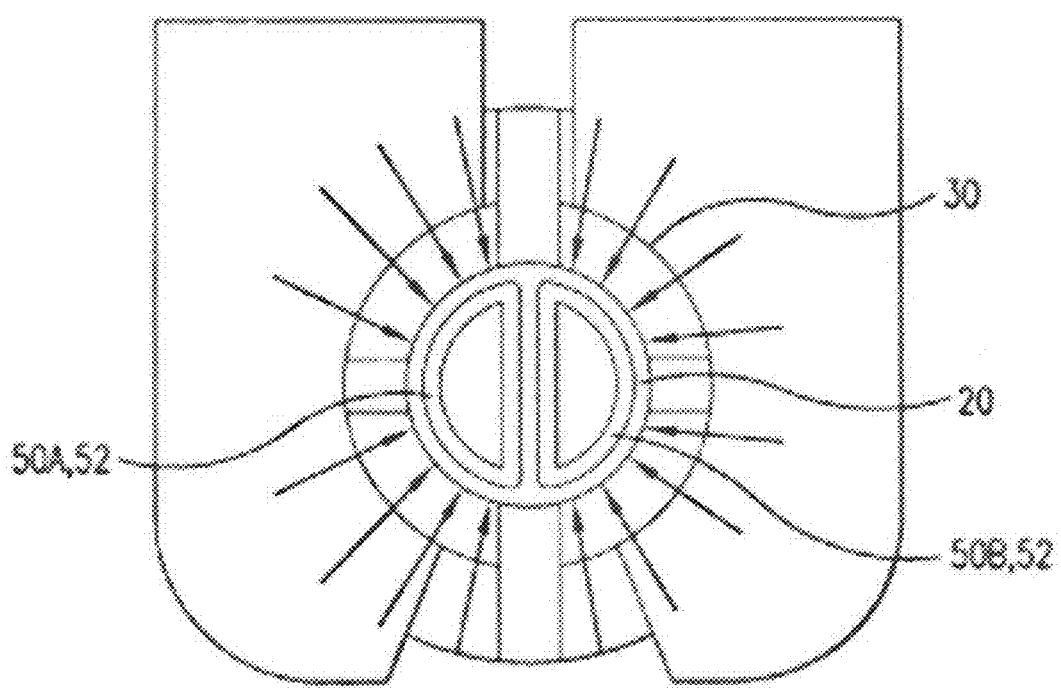
FIG. 28 is a schematic view of the snap clip locking mechanism.

A tenth embodiment of the catheter 10 of the present invention is illustrated in FIGS. 28-29. In this aspect, the catheter comprises a hub member 30 having a snap clip locking mechanism 200 for securing the hub member relative to the catheter tube 20 and the hemostasis taper sleeve 110. In one aspect, the hub member 30 of the catheter comprises an embedded cutting assembly 80, such as, for example, a razor blade, that is positioned rearwardly of the first ends 52 of the attachment tubes to which the lumens 26A, 26B of the dual lumen catheter are drawn over. The cutting assembly 80 is configured to cut away the excessive length of the catheter tube, i.e., to trim away the portion of the catheter tube that have passed beyond the first end portions of the attachment tubes.

In one aspect, the snap clip locking mechanism 200 is configured to be slideably mounted thereon a portion of the hub member 30 and is movable between a disengaged position and an engaged position. In the engaged position, compression is applied onto the hemostasis taper sleeve 110, the underlying catheter tube 20, and the underlying attachment tubes 50 to form a secure fluid tight connection. In another aspect, the waste portions 28 of the catheter tube may be drawn out of an opening 202 defined in a portion of the hub member. In another aspect, the hub member 30 can also include a hinged door 204 that covers the opening after the snap clip locking mechanism is positioned in the engaged position.

In this aspect, the lumens of the catheter tube are pre-attached to the first end portions of the attachment tubes mounted therein the hub member. The length of the catheter lumen is trimmed to the desired length via the embedded cutting assembly in the hub member, which cuts the catheter as it is slideably drawn past the cutting assembly. In operation, the formed waste catheter tube is trimmed or cut off and the hub member is connected to the hemostasis taper sleeve via a portion of the snap clip locking mechanism when the locking mechanism is positioned in the engaged position.

In one aspect, the snap clip locking mechanism provides the compression needed to seal the catheter and cuts off the waste catheter as it is engaged. In another aspect, the attachment tubes of the catheter are in fluid communication with the extension tubes of the catheter.

Referring now to FIGS. 29 and 30A-30D, also presented herein is a repair kit 200 for repairing a catheter and a method of repairing a catheter using the catheter repair kit. The repair kit 200 may be used to repair many different types of catheters, such as, but not limited to, dialysis catheters, peripherally inserted central catheters (PICCs), central venous catheters (CVCs) or any other implanted catheter with exposed catheter tubing. It is common that over time and with extended use an implanted catheter may weaken or break causing stress points in the catheter shaft or the extension tubes. The most common areas that may need repair on an implanted catheter are typically the extension legs, clamps, luer ends, or any exposed viable tubing of the catheter shaft. For example, a clamp, over time and with repeated use, may create indentations on the extension legs which may lead to a wear or stress point. Such a wear or stress point means the weakened area of the extension leg tubing may eventually break or not return to normal diameter. Typically, if such a wear or stress point develops, a practitioner may want to cut the extension leg at a point distal of the stress or wear point, and replace the damaged tubing with a replacement extension tube. Additional examples of wear and stress include the use of chemicals and other medicinal agents to clean the catheter before or after dialysis may damage the integrity of the exposed portions of the catheter. Moreover, the clamps and fittings on the extension legs may need to be repaired due to extended use, normal wear and tear resulting from usage, or being handled by nurses or physicians during routine use. These examples of damage to a catheter are not intended to limit the type of damage or repairs that this repair device 200 is capable of repairing. One solution currently used by physicians to repair a damaged implanted catheter is to replace the entire catheter which means additional and invasive medical procedures for the patient. By using this repair kit 200 to replace the defective component of the catheter, the physician may avoid having to replace the entire catheter.

The repair kit 200 may be used to repair or replace any exposed tubing of an implanted catheter. For example, the repair kit 200 may repair or replace a broken or damaged remnant extension leg 220, damaged clamp 273, damaged fitting 276 or in an alternative embodiment (not shown) a damaged exposed catheter shaft of a single lumen implanted catheter.

As illustrated in FIG. 29, in one exemplary aspect, the catheter repair kit 200 may comprise at least one delivery rod 201, at least one connection element 210, and at least one replacement extension tube 230. The replacement extension tube 230 is further comprised of at least one fitting 240, such as a standard luer fitting, at its proximal most end, at least one replacement clamp 246, and replacement catheter tubing 243 attached to the fitting 240. A sealing ring 235 can be positioned within a portion of the lumen 242 of the replacement catheter tube 243. Also depicted in FIG. 29 is a partial view of the distal segment of an implanted catheter showing a remnant extension leg 220 with proximal end 221. The remnant extension leg 220 has been trimmed or cut prior to repair in order to remove any damaged segment. The remnant extension leg 220 is the remaining viable section of extension leg tubing distal to the break or weak point after the user has trimmed or cut the damaged area. The extension legs 220 and 270 extend from catheter hub 225, which is depicted in plan view for clarity.

The connection element 210, seen more clearly in FIG. 30A-30D is configured to effect a fluid-tight connection between the lumen 242 of the replacement extension tube 230 and the lumen 222 of the remnant extension leg 220. The connection element 214 has a proximal end 211 and a distal end 213. The connection element 214 has a lumen 213 which allows for open fluid communication between the lumen 242 of the replacement extension tube 230 and the lumen 222 of the remnant extension leg 220. Also, the connection element 214 has a proximal end, a distal end, and an outer surface that is capable of being coupled to a portion of the inner wall of both the remnant extension leg 220 and the replacement extension tube 230. The outer surface of the connection element 214 may have multiple shapes and dimensions depending on the specific type of catheter in need of repair. For example, the connection element 214 may be comprised of a bi-directional barb 210 configuration so that the outer surface of the connection element has multiple barbs 210. In this aspect, the bi-directional multiple barbed 210 connection element 214 comprises at least one barb 210 facing in a first distal direction on a distal portion 212 of the connection element 210, and at least one barb 210 facing in the opposite direction on a proximal portion 211 of the connection element 214 as shown in FIG. 29, and FIGS. 30A-30D. These barbs 210 are configured to resist movement in both directions. Furthermore, the outer surface of each barb 210 may be coupled to a portion of the inner wall of the replacement extension tube 230 and a portion of the inner wall of the remnant extension leg 220. The connection element 214 may be comprised of materials such as, but not limited to, titanium, nitinol and steel, polyetherimides such as ultem, rigid polyurethanes such as ispolast, PEEK, poly sulfone, poly acetal, and polycarbonate such as Lexan.

When used to repair damaged dialysis catheters, the minimum inner diameter of the lumen 213 of the connection element 214 may be about 0.135 inches, although other dimensions are acceptable as long as the lumen 213 is dimensioned to allow the flow of fluid through the lumen of the dialysis catheter. In one embodiment, the outer diameter of the connection element 214 used with dialysis catheters may be a minimum of about 0.005 inches greater than the inner diameter of the remnant extension leg 220, although other dimensions are acceptable as long as the connection element is immovably secured to the tubing of the remnant extension leg 220. For example, if the remnant extension leg 220 has an inner diameter of about 0.135 inches then the minimum outer diameter of the connection element 214 may be about 0.140 inches.

Furthermore, when the repair kit 200 is used to repair a damaged PICC, the inner diameter of the lumen 213 of the connection element 214 could be about 0.020 inches, although other dimensions are acceptable as long as the PICC is dimensioned to allow fluid flow through the lumen of the PICC. The outer diameter of the connection element 214 used with PICCs may be about 0.100 inches, or a minimum of at least about 0.005 inches greater than the inner diameter of the remnant extension leg 220, although other dimensions of the outer diameter of the connection element 214 used with PICCs are acceptable as long as the connection element is immovably secured to the tubing. The length of the connection element 214 may be between about 0.25 inches and 0.75 inches if it is used to replace the damaged extension leg of either PICCs or dialysis catheters.

The delivery rod 201 may be configured to facilitate insertion of the connection element 214 into a portion of the lumen 222 of the remnant extension leg 220 or, in an alternative embodiment, the lumen of the exposed viable catheter shaft (not shown). The rod 201 may also be used to aid in positioning the replacement extension tube 230 during repair. The rod 201 has both a proximal end and a distal end 209. The distal end 209 of the delivery rod 201 may be attached, coupled, or releasably coupled, to the connection element 210. The proximal end of the delivery rod 201 may be inserted through the distal end opening 245 into the lumen 242 of the replacement extension tube 230 and extend proximally beyond the proximal most end of the luer fitting 240, as shown in FIG. 30B. The rod 201 may be comprised of materials such as, but not limited to, steel or nitinol, plastic, or other flexible and solid materials known in the art. Additionally, the rod 201 may be made from a tubing material, such as hypo-tubing, that in addition to being flexible and solid, also comprises a lumen. In one embodiment, the outer diameter of the rod 201 can be less than the inner diameter of the lumen 242 of the replacement extension tube 230 and the lumen of sealing ring 235 so that the entirety of the rod 201 can be coaxially slideable relative to the lumen 242 of the replacement extension tube 230 and the lumen of the sealing ring 235.

The distal end 209 of the rod 201 may be releasably coupled to the connection element 214 through either an interference fit or a releasable locking mechanism (not shown). To create such an interference fit between the distal end 209 of the rod 201 and the connection element 210, the outer diameter of the distal end 209 of the rod 201 may be slightly larger than the outer diameter of the lumen 213 of the connection element 210. It is also possible to have a series of different types of releasable locking mechanisms. For example, the rod 201 and connection element may be releasably coupled by the distal end 209 of the rod 201 having a raised bump or dimple (not shown) that creates an interference fit within the lumen 213 of the connection element 210. An example of a releasably locking mechanism may be if the distal end 209 of the rod 201 and lumen 213 of the connection element 214 may contain threads so that the rod 201 may be screwed into the connection element 210. Additionally, another example is if a raised bump on the distal end 209 of the rod 201 and an insert within the lumen 213 of the connection element 214 may be used to twist and lock the rod 201 in place. Further examples of such releasable locking mechanisms include a thin section of plastic material disposed at the distal end of 212 of the connection element 214 which is configured to break when sufficient force is applied to the rod 201 in a proximal or distal direction. Yet another example is a split and slightly flared distal end 209 of the rod 201, comprised of hypo-tubing. The flare would be sufficient to allow the connection element 214 to be pulled proximally into the lumen 242 of the replacement catheter tubing 230, but when enough force is applied proximally the flared distal end of the hypo tubing rod 201 would collapse inward and allow the rod 201 to be removed from the replacement end 230.

The connection element 214 and rod 201 may be pre-assembled as part of the entire repair kit 200. In additional embodiments the rod 201 and connection element 214 are not pre-assembled because the repair kit 200 may comprise different types of rods 201 and different types of connection elements 210 which may be used interchangeably. For example, the repair kit 200 may come with 4 or 5 different sized and shaped connection elements 210 that all could be used with a single rod 201, allowing the end user to select the connection element 214 that will work the best for the catheter being repaired. Assembling the rod 201 and connection element 214 will depend on the type of releasably coupled connection. For example, if the rod 201 and connection element 214 are to be coupled through an interference fit, but are not preassembled, force may need to be applied distally on the rod 201 to insert the distal end 209 of the rod 201 into a portion of the lumen 213 of the proximal portion 211 of the connection element 210.

The replacement extension tube 230 is configured to replace the damaged or broken portion of an extension leg 270 with replacement catheter tubing 243, a replacement clamp 246, and a replacement fitting 240. The replacement extension tube 230 is comprised of a fitting 240, such as a standard luer fitting, on its proximal most end and replacement catheter tubing 243 attached thereon. The replacement clamp 246 may be positioned or placed in a surrounding relationship to the outer surface of the replacement catheter tubing 243. The replacement extension tube 230 has a distal end opening 245, a proximal end, a distal end, and an outer surface. In one embodiment, a sealing ring 235 may be positioned within a portion of the lumen 242 of catheter tubing 243, however, in additional embodiments no sealing ring 235 may be required.

In another embodiment (not shown), the replacement extension tube 230 may be used to replace the damaged or broken portion of the exposed shaft of a single lumen catheter near the hub or any portion distal to the damaged area but proximal to the insertion site. The exposed shaft of a single lumen catheter refers to the portion of the catheter shaft which is proximal to the insertion site on the patient's body, and at least a portion of the catheter shaft distal to the hub is not under the skin, or implanted within, the body of the patient. The replacement extension tube 230 in this additional embodiment (not shown) can be configured to replace the damaged exposed catheter shaft, a hub connection, replacement catheter tubing, a replacement clamp, and a fitting. Additionally, in this additional embodiment (not shown) the replacement catheter tube will further comprise of a hub connection (not shown) on its outer surface that may be used to suture, stick, or attach the replacement catheter tubing 243 to the skin of the patient.

The replacement catheter tubing 243 may be comprised of materials such as, but not limited to, biocompatible polymers, including silicone, polyurethane, low density polyethylene, high density polyethylene, and/or any other similar materials or combinations typically known or used in the art. Additionally, any materials used to make the replacement catheter tubing 243 may be elastomeric causing it to neck down, collapse, or grip a portion of the sealing ring 235, connection element 210, or remnant extension leg 220 within its lumen 242. This means that the replacement catheter tubing 243 may be manufactured from such materials that prevent the sealing ring 235, connection element 210, or remnant extension leg 220 from being pulled out of lumen 242 after installation of a repair device. The fitting 240, such as a luer end, of the replacement extension tube 230 is also standard in the art. The sealing ring 235 can be configured to ensure that a portion of the outer surface of the connection element 214 has a secure and leak-proof, fluid-tight fit with a portion of the inner wall of replacement catheter tubing 243. In one embodiment, the inner wall of the replacement catheter tubing 243 creates an interference fit with the outer wall of the sealing ring 235. In this embodiment, after the connection element 214 has been inserted and repair is complete, an interference fit is created between the outer wall of the connection element 214 and both inner wall of the sealing ring 235 and the inner wall of the remnant extension leg 220. The sealing ring 235 can be made from a number of different materials, such as, but not limited to those described above for catheter tubes. In an additional embodiment, there may be no need for a sealing ring 235 and instead the outer diameter of the connection element 214 and remnant extension leg 220 are equal or at least about 0.005 inches greater than the lumen 242 of the replacement catheter tubing 243, thus creating the desired interference fit.

Furthermore, the replacement tubing 243, replacement clamps 246, and replacement fittings 240 of the repair kit 200 may be labeled, color coded, or otherwise customized to further identify its use with the currently implanted catheter. For example, if the currently implanted catheter has multiple extension legs and each have a specific flow rate, and only one of these extension legs need to be replaced, this repair kit 200 may be customized to identify the specific flow rate for the replaced extension leg.

A key advantage to this repair kit 200 is that only a very small amount of exposed remnant extension leg 220 or viable catheter shaft (not shown) needs to remain distal to the removed damaged area. Some current repair systems require that the broken or damaged extension legs have a minimum length of viable extension tubing, for example at least 3-5 cm. This repair kit 200 solves such a problem because after removal of the damaged catheter area the remaining remnant extension leg 220 or exposed viable catheter shaft (not shown) may only need to be a length equal to the distal portion 213 of the connection element 210, or about half the length of the total connection element 210. For example, if the length of the connection element 214 is between about 0.25 inches and about 0.75 inches, the required length of the remnant extension leg 220 or exposed viable catheter shaft (not shown) would need to be between about 0.125 inches and about 0.375 inches, which is approximately the length of the distal end 212 of the connection element 214 or half the total length of the connection element 210.

Figure 30A:
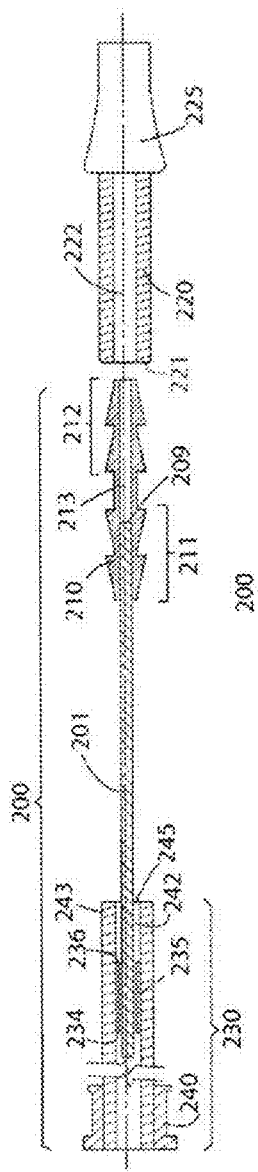
FIG. 30A-D illustrate a method of using the repair kit to repair an implanted catheter.
Figure 30B:
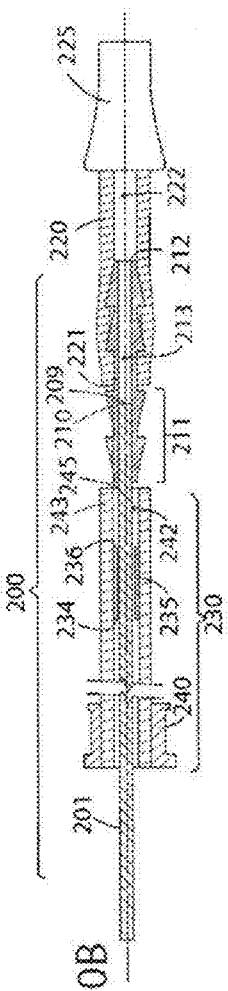

The method of repairing a damaged extension leg 220, damaged clamp 246, 273, damaged luer fitting 140, or damaged exposed catheter shaft of a single lumen implanted catheter (not shown) is described herein with reference to FIGS. 30A-30D. A catheter hub 225 is shown in plan view for clarity. FIG. 30A illustrates a cross-sectional view of the extension leg of a single lumen implanted catheter and the repair kit 200 prior to repair. Also shown is the repair kit 200 with a rod 201 and connection element 210, a replacement fitting 240, and a replacement tubing 243 with a sealing ring 235 in lumen 242. Additionally, the proximal end of the delivery rod 201 is positioned within a portion of lumen 242 of the replacement extension tube 230 and extends out from the distal end of replacement catheter tubing 243. The remnant extension leg 220 has been cut distal to the damaged area on the extension tube leaving an exposed cut end 221.

If the repair kit 200 does not come with the rod 201 and connection element 214 pre-assembled then the user must first couple the distal end 209 of the rod 201 with the lumen 213 of the connection element 210. If the connection element 214 and rod 201 are not pre-assembled, the end user has the ability to choose different shaped and sized connection elements 210 depending on the extension tub or catheter being repaired.

As shown in FIG. 30B, the user first inserts the distal portion 212 of the connection element 214 within a portion of the lumen 222 of the already cut or trimmed remnant extension leg 220 at the exposed cut end 221. Depending on the type of releasably coupled attachment being used, either an interference fit or a releasably locking mechanism, the connection element 214 may or may not be positioned over delivery rod 201. For example, in one embodiment an interference fit is used to couple the rod 201 and connection element 210, and in this embodiment the connection element 214 will be positioned over the distal end 209 of the rod 201. The rod 201 may be used to facilitate advancement and positioning of the connection element 214 within a portion of the lumen 222 of the remnant extension leg 220. In the embodiment shown in FIG. 30B, the user may then insert the distal portion 212 of the connection element 214 within a portion of the lumen 222 of the remnant extension leg 220. When the distal portion 212 of the connection element 214 is within a portion of the lumen 222 of the remnant extension leg 220 then the proximal portion 211 of the connection element 214 may be placed within a portion of the lumen 242 of the distal end 245 of the replacement catheter tubing 243. When the distal end 212 of the connection element 214 is sufficiently advanced within a portion of lumen 222 of the remnant extension leg 220 the outer surface of the connection element 214 will create an interference fit with a portion of the inner wall of tubing 220. In the embodiment shown in FIG. 30B, the outer surface of the 210 connection element comprises at least one bi-directional barb element 210 which is coupled to the inner wall of the remnant extension leg 220 and the inner wall of the replacement extension tube 230. During the insertion step, replacement extension tube 230 may be positioned in slideably coaxial relationship to delivery rod 201 as shown in FIG. 30B or alternatively, may be advanced over rod 201 after insertion of the rod into the remnant extension leg 220.

Figure 30C:
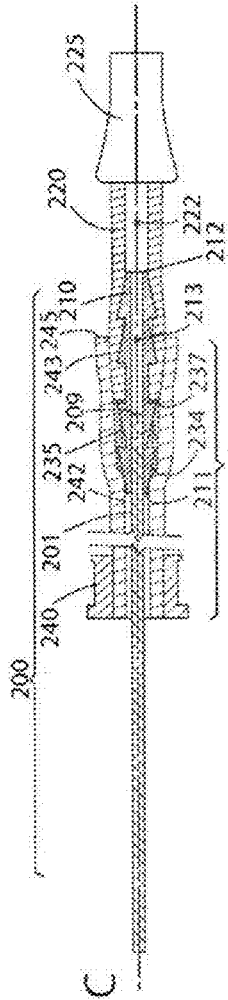
Figure 30D:
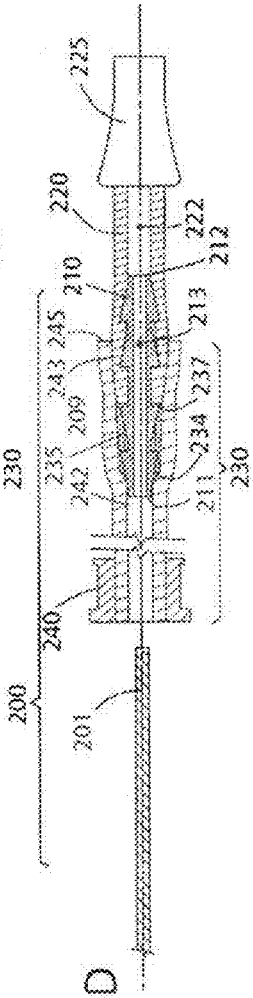

As seen in FIG. 30C, to connect the replacement extension tube 230 to the remnant extension leg 220, the user may pull rod 201 proximally to draw remnant extension leg 220 and the proximal portion 211 of the attached connection element 214 into the lumen 242 of the replacement catheter tubing 243. The user may also simultaneously or subsequently advance the replacement extension tube 230 distally over the delivery rod 201 until a portion of the outer wall of the connection element 214 is positioned within sealing ring 235, creating an interference fit. Such an interference fit ensures a fluid-tight connection or seal between the outer surface of the connection element 214 and the inner surface of both the lumen 242 of the replacement extension tube 230 and the lumen 222 of the remnant extension leg 220. As seen in FIG. 30D, the distal end 245 of the replacement extension tube 230 has been positioned over the outer wall of the proximal end 221 of the remnant extension leg 220, and the connection element 214 is positioned within the a portion of lumen 242 of the replacement extension tube 230 and the lumen 222 of the remnant extension leg 220. The proximal end 221 of the remnant extension tube 220 may be coupled with the open distal end 245 of the replacement extension leg 243.

Next, the rod 201 may be released from the connection element 210. To release or disconnect the rod 201 the user may sever or break the connection with the connection element 210. Depending on how the rod 201 and connection element 214 are coupled, the user will either activate the releasable locking mechanism on the rod 201 or apply force to release any interference fit between the rod 201 and the connection element 201. Once the rod 201 and connection element 214 have been separated, severed or disconnected, from their coupled state, the user will pull the rod 201 proximally until the entire rod 201 is removed from the device 200, as illustrated in FIG. 30D. Once the rod is removed, a through channel for fluid flow is created. As described above, the rod 201 may be made from material such as hypo tubing which has a through lumen. In this embodiment, the user may not need to remove the rod 201 in order to create a desired through channel for fluid flow. The fluid flow created by the through channel will have an open and continuous fluid communication that starts at the fitting 140, goes through the lumen 242 of the replacement extension tube 230 into the lumen 213 of the connection element 210, through the lumen 222 of the remnant extension tube 220, entering into the hub 225 and traveling the selected distance of the remaining implanted catheter lumen (not shown).

In the one embodiment, the rod 201 may be solid which may prevent blood from entering or exiting through the implanted catheter during installation and this may assist in preventing air embolisms. However, in an alternative embodiment (not shown) the repair kit 200 comprises of a balloon catheter and a hollow delivery rod 201. In such an alternative embodiment (not shown), the balloon catheter is used in combination with the hollow delivery rod 201 to prevent or decrease the likelihood of air embolisms during the repair process. After the delivery rod 201 and connection element 214 have been placed within the lumen 222 of the remnant extension leg 220, as described above, the balloon catheter may be inserted in the proximal most end of the hollow rod 201. The balloon catheter will be advanced in the lumen of the hollow delivery rod 201 until the distal most end of the balloon catheter is distally beyond the distal end 213 of the connection element 214 and within the lumen 222 of the remnant extension leg 220. Next, a syringe at the proximal most end of the balloon catheter may inflate the balloon. The inflated balloon may prevent air from entering into a patient's blood stream and thus aid in preventing air embolisms. Next, the replacement extension tube 230 may be placed over the outer wall of the hollow delivery rod 201 and secured to the proximal end 211 of the connection element 214 as described above. After the replacement extension tube 230 is secured in place, the balloon may be deflated and removed from the lumen of the hollow delivery rod 201.

The repair kit 200 may come pre-assembled with different components. For example, a typical repair kit 200 may be comprised of a rod 201, connection element 210, replacement extension tube 230 further comprising a luer 240, clamp 246, and replacement catheter tubing. Additionally, the pre-assembled kit may include scissors (not shown), safety slide clamp (not shown), adhesive drape (not shown), and priming volume and site care label (not shown).

The preceding description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. The corresponding structures, materials, acts, and equivalents of all means or step plus function elements in the claims below are intended to include any, structure, material, or acts for performing the functions in combination with other claimed elements as specifically claimed.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Accordingly, those who work in the art will recognize that many modifications and adaptations to the present invention are possible and can even be desirable in certain circumstances and are a part of the present invention. Other embodiments of the invention will be apparent to those skilled in the art from consideration of the specification and practice of the invention disclosed herein. Thus, the preceding description is provided as illustrative of the principles of the present invention and not in limitation thereof. It is intended that the specification and examples be considered as exemplary only, with a true scope and spirit of the invention being indicated by the following claims.

What is claimed is:

1. A method for repairing a catheter, wherein the method comprises:
   providing a catheter having at least one remnant extension leg;
   providing a repair kit, wherein the repair kit comprises:
      a rod having a proximal end and a distal end, wherein the distal end of the rod is coupled to a connection element having a proximal end and a distal end, a lumen and an outer surface;
      a replacement extension tube comprising a proximal end and a distal end, a lumen, an outer surface, and a fitting coupled to the proximal end of the replacement extension tube;
   attaching at least a portion of the distal end of the connection element to at least a portion of the remnant extension leg;
   coupling the remnant extension leg to the replacement extension leg; and
   removing the rod from the repair kit.

2. The method of claim 1, wherein before the step of attaching, the method further comprises:
   providing a clamp configured to be positioned in surrounding relationship to at least a portion of the outer surface of the replacement extension tube; and
   positioning the clamp around at least a portion of the outer surface of the replacement extension tube.

3. A method for repairing a catheter, wherein the method further comprises:
   providing a catheter having at least one remnant extension leg;
   providing a rod having a proximal end and a distal end, wherein the distal end of the rod is coupled to a connection element having a proximal end and a distal end;
   attaching at least a portion of the distal end of the connection element to at least a portion of the remnant extension leg;
   coupling the remnant extension leg to the replacement extension leg; and
   removing the rod from the repair kit.

4. A method for repairing a catheter, wherein the method comprises:
   providing a catheter having at least one exposed catheter shaft;
   providing a repair kit, wherein the repair kit comprises:
      a rod having a proximal end and a distal end, wherein the distal end of the rod is coupled to a connection element having a proximal end and a distal end, a lumen and an outer surface;
      a replacement extension tube comprising a proximal end and a distal end, a lumen, an outer surface, and
      a fitting coupled to the proximal end of the replacement extension tube;
   attaching at least a portion of the connection element to at least a portion of the exposed catheter shaft;
   coupling the exposed catheter shaft with the replacement extension leg; and
   removing the rod from the repair kit.

* * * * *